United States Patent
Jalan et al.

(10) Patent No.: US 11,752,196 B2
(45) Date of Patent: Sep. 12, 2023

(54) TREATMENT OF PYROPTOSIS

(71) Applicants: Rajiv Jalan, London (GB); Ugo Soffientini, London (GB); Nigel Beaton, London (GB); Gautam Mehta, London (GB)

(72) Inventors: Rajiv Jalan, London (GB); Ugo Soffientini, London (GB); Nigel Beaton, London (GB); Gautam Mehta, London (GB)

( * ) Notice: Subject to any disclaimer, the term of this patent is extended or adjusted under 35 U.S.C. 154(b) by 0 days.

(21) Appl. No.: 17/026,534

(22) Filed: Sep. 21, 2020

(65) Prior Publication Data
US 2021/0069296 A1 Mar. 11, 2021

Related U.S. Application Data

(63) Continuation of application No. PCT/GB2019/050814, filed on Mar. 21, 2019.

(30) Foreign Application Priority Data

Mar. 21, 2018 (GB) ..................................... 1804514

(51) Int. Cl.
| | | |
|---|---|---|
| A61K 38/17 | (2006.01) | |
| A61P 1/16 | (2006.01) | |
| A61K 31/27 | (2006.01) | |
| A61K 31/277 | (2006.01) | |
| A61K 38/07 | (2006.01) | |
| A61K 45/06 | (2006.01) | |
| G01N 33/68 | (2006.01) | |

(52) U.S. Cl.
CPC .......... *A61K 38/1793* (2013.01); *A61K 31/27* (2013.01); *A61K 31/277* (2013.01); *A61K 38/07* (2013.01); *A61K 38/1709* (2013.01); *A61K 45/06* (2013.01); *A61P 1/16* (2018.01); *G01N 33/6893* (2013.01); *G01N 2800/085* (2013.01)

(58) Field of Classification Search
CPC ....... A61K 38/17; A61K 38/1709; A61P 1/16; G01N 2800/085
See application file for complete search history.

(56) References Cited

U.S. PATENT DOCUMENTS

| | | |
|---|---|---|
| 5,503,978 A | 4/1996 | Schneider et al. |
| 5,567,588 A | 10/1996 | Gold et al. |
| 5,654,151 A | 8/1997 | Allen et al. |

FOREIGN PATENT DOCUMENTS

| | | |
|---|---|---|
| WO | 96/38579 A1 | 12/1996 |
| WO | 99/57273 A3 | 11/1999 |

OTHER PUBLICATIONS

Khanova et al. ("Pyroptosis by Caspase 11/4-Gasdermin-D Pathway in Alcoholic Hepatitis in Mice and Patients", Hepatology, published online Feb. 27, 2018, pp. 1737-1753) (Year: 2018).*
Qiu et al. ("'Hints' in the killer protein gasdermin D: unveiling the secrets of gasdermins driving cell death", Cell Death and Differentiation, 2017, pp. 588-596) (Year: 2017).*
Abe et al. (Pyroptosis as a Regulated Form of Necrosis Pl+/Annexin V-/High Caspase 1/Low Caspase 9 Activity in Cells = Pyroptosis?, Circ Res. 2016, 1457-1460) (Year: 2016).*
Gupta et al. ("Production of Recombinant Pharmaceutical Proteins." Basic and Applied Aspects of Biotechnology, 2016, 77-101). (Year: 2016).*
Adebayo et al., Mechanism of cell death in acute-on-chronic liver failure: A clinico-pathologic-biomarker study. Liver Int. 2015; 35:2564-74.
Antoine et al., Molecular forms of HMGB1 and keratin-18 as mechanistic biomarkers for mode of cell death and prognosis during clinical acetaminophen hepatotoxicity. J Hepatol. 2012; 56:1070-1079.
Björnsson et al., Clinical characteristics and prognostic markers in disulfiram-induced liver injury. J Hepatol. 2006; 44(4):791-797.
Carl et al., A model of acute kidney injury in mice with cirrhosis and infection. Liver Int. 2016; 36(6):865-73.
Gao and Wells, Identification of Specific Tethered Inhibitors for Caspase-5, Chemical Biology and Drug Design. Chem. Biol. Drug Des. 2012; 79(2):209-215.
Gehrke et al., Hepatocyte-specific deletion of IL1-RI attenuates liver injury by blocking IL-1 driven autoinflammation. J. Hepatol. 2018; 68(5):986-995.
Guo et al., The relevance of pyroptosis in the pathogenesis of liver diseases. Life Sciences 2019; 223:69-73.
Hall et al., Sample size requirement for digital image analysis of collagen proportionate area in cirrhotic livers. Histopathology 2013; 62(3):421-30.

(Continued)

*Primary Examiner* — Lianko G Garyu
(74) *Attorney, Agent, or Firm* — Kilpatrick Townsend Stockton LLP

(57) ABSTRACT

The present invention derives from the unexpected finding that pyroptosis is a novel biomarker and target for therapy in liver failure such as acute liver failure (ALF) and acute-on-chronic liver failure (ACLF). Gasdermin D (GSDMD), caspase 4, caspase 5, or Interleukin 1 alpha (IL-1α) can be detected and quantified in serum or plasma, and used as biomarkers for outcome in liver failure such as acute liver failure (ALF) and ACLF and other diseases involving aberrant pyroptosis. By antagonising GSDMD, caspase 4, caspase 5 or Interleukin 1 alpha (IL-1α) many of the unwanted consequences or symptoms of liver failure such as acute liver failure (ALF) and acute-on-chronic liver failure (ACLF) may be reduced. The present invention utilises these findings to identify and provide antagonists of GSDMD, caspase 4, caspase 5 or IL-1α that may be used in the treatment or prevention of liver failure such as acute liver failure (ALF) and ACLF. The present invention utilises these findings to identify and provide antagonists of GSDMD, caspase 4, caspase 5 or IL-1α that may be used in the treatment or prevention of aberrant pyroptosis in the kidney, brain, liver or other organ of the body.

6 Claims, 16 Drawing Sheets

(56) References Cited

OTHER PUBLICATIONS

Hu et al., Identification of pyroptosis inhibitors that target a reactive cysteine in gasdermin D. bioRxiv Jul. 10, 2018; https://doi.org/10.1101/365908 [Preprint], 37 pages.
International Search Report issued in connection with corresponding International Application No. PCT/GB2019/050814, dated Aug. 9, 2019, 2 pages.
Jalan et al., Acute-on chronic liver failure. J. Hepatol. 2012; 57(6):1336-1348.
Khanova et al., Pyroptosis by caspase 11/4-gasdermin-D pathway in alcoholic hepatitis in mice and patients. Hepatology 2018; 67(5):1737-1753.
Maddox et al., Elevated serum levels in human pregnancy of a molecule immunochemically similar to eosinophil granule major basic protein. J. Exp. Med. 1983; 158 (4):1211-1226.
Marmarou et al., An improved gravimetric measure of cerebral edema. J. Neurosurg. 1982; 56:246-53.
Sukriti et al., Microvesicles in hepatic and peripheral vein can predict nonresponse to corticosteroid therapy in severe alcoholic hepatitis. Aliment. Pharmacol. Ther. 2018; 47:1151-61.
Wang et al., Murine Caspase-11, an Ice-Interacting Protease, Is Essential for the Activation of Ice. Cell 1998; 92:501-509.
Yang et al., Mechanism of gasdermin D recognition by inflammatory caspases and their inhibition by a gasdermin D-derived peptide inhibitor. PNAS 2018; 115:6792-6797.
Arroyo et al., Acute-on-Chronic Liver Failure. N Engl J Med 2020;382:2137-45.
Gustot et al., Transition to decompensation and acute-on-chronic liver failure: Role of predisposing factors and precipitating events. Journal of Hepatology 2021, vol. 75, S36-S48.
Lin et al., Defining the prognosis of critically ill patients with alcohol-related liver disease. Journal of Hepatology 2021, vol. 75, 986-987.
Moreau et al., Acute-on-Chronic Liver Failure Is a Distinct Syndrome That Develops in Patients with Acute Decompensation of Cirrhosis. Gastroenterology 2013, vol. 144, No. 7, 1426-1437.

* cited by examiner

Fig. 3

|  | Decompensated cirrhosis (DC) n=7 | Acute-on-Chronic Liver Failure (ACLF) n=6 | p-value (DC vs ACLF) |
|---|---|---|---|
| Age [mean (SD)] | 55.9 (6.0) | 54.5 (10.4) | p =0.78 |
| Male [n (%)] | 5 (71.4) | 4 (66.7) | p =0.73 |
| Aetiology [n (%)] |  |  |  |
| Alcohol | 1 (25.0) | 1 (16.7) | p =0.87 |
| NASH | 1 (0) | 2 (33.3) |  |
| Alcohol + NASH | 1 (12.5) | 1 (16.7) |  |
| Alcohol + HCV | 3 (50.0) | 1 (16.7) |  |
| Other | 1 (12.5) | 1 (16.7) |  |
| Bilirubin [mean (SD)] | 1.7 (1.0) | 12.6 (6.5) | p <0.01* |
| INR [median (IQR)] | 1.4 (1.3-1.5) | 3.1 (2.3-3.9) | p <0.01* |
| Creatinine | 1.0 (0.2) | 2.5 (1.7)* | p <0.05* |
| MELD score | 12.6 (2.4) | 35.3 (7.9) | p <0.01* |
| CLIFC-ACLF score | 32.7 (3.4) | 58.6 (9.9) | p<0.01* |

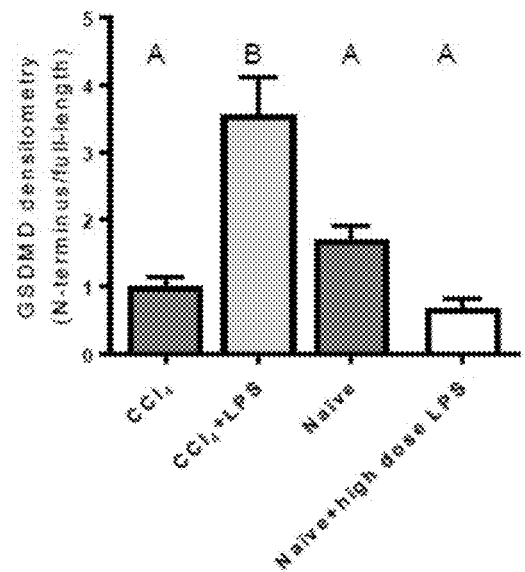

Untreated Huh7        Huh7 + FITC-LPS

TREATMENT OF PYROPTOSIS

FIELD OF THE INVENTION

The present invention derives from the unexpected finding that pyroptosis is a novel biomarker and target for therapy in liver failure such as acute liver failure (ALF) and acute-on-chronic liver failure (ACLF).

Gasdermin D (GSDMD), caspase 4, caspase 5, or Interleukin 1 alpha (IL-1α) can be detected and quantified in serum or plasma, and used as biomarkers for outcome in liver failure such as ALF and ACLF and other diseases involving aberrant pyroptosis.

By antagonising GSDMD, caspase 4, caspase 5 or Interleukin 1 alpha (IL-1α) many of the unwanted consequences or symptoms of acute liver failure (ALF) and/or acute-on-chronic liver failure (ACLF) may be reduced.

The present invention utilises these findings to identify and provide antagonists of GSDMD, caspase 4, caspase 5 or IL-1α that may be used in the treatment or prevention of liver failure such as ALF and ACLF.

The present invention utilises these findings to identify and provide antagonists of GSDMD, caspase 4, caspase 5 or IL-1α that may be used in the treatment or prevention of aberrant pyroptosis in the kidney, brain, liver or other organ of the body.

BACKGROUND TO THE INVENTION

An acute decompensating event ((AD), bacterial infection, large-volume ascites, GI haemorrhage, or hepatic encephalopathy, alone or in combination) is the most common hospital presentation of cirrhotic liver disease and can be successfully managed in most cases. However, 30% of patients present with or develop rapidly progressive hepatic and/or extra-hepatic organ failure, a condition referred to as acute-on-chronic liver failure (ACLF). About 20% of these patients progress to multi-organ failure and death. There are currently no specific treatments for ACLF.

Acute-on-chronic liver failure (ACLF) affects about 1 in 3 patients hospitalised with a complication of cirrhosis, and has a 28-day mortality>30%. The pathobiology of ACLF is characterised by translocation of gut-derived bacteria and bacterial products (such as lipopolysaccharide—LPS) to the liver via portal blood, promoting pro-inflammatory responses through the TLR4-dependent canonical inflammasome on immune cells, as well as the TLR4-independent non-canonical inflammasome in hepatocytes.

ACLF is diagnosed by use of the Chronic Liver Failure (CLiF) Consortium criteria, NACSELD criteria or APASL criteria. Previously validated scores to assess disease severity include Child-Pugh (CP) classification, Model for End Stage Liver Disease (MELD) and the CLiF Consortium Acute Decompensation (CLIF-C AD) score.

Pyroptosis is a highly inflammatory form of programmed cell death that occurs both from sterile inflammation and also upon infection with pathogens. In this process, immune cells recognize foreign danger signals within themselves, release pro-inflammatory cytokines, swell, burst and die. The released cytokines attract other immune cells and contribute to inflammation in the tissue. Cell death by pyroptosis results in plasma-membrane rupture and the release of damage-associated molecular pattern (DAMP) molecules such as ATP, DNA and ASC oligomers (specks) into the extracellular milieu, including cytokines that recruit more immune cells and further perpetuate the inflammatory cascade in the tissue.

SUMMARY OF THE INVENTION

Acute-on-chronic liver failure (ACLF) displays systemic inflammation and non-apoptotic hepatocyte cell death. Caspase 4/5 is activated in hepatocytes, leading to the cleavage of Gasdermin D (GSDMD), a mediator of pyroptotic cell death. Upon cleavage, GSDMD forms pores in the cell membrane leading to cell death and release of DAMPs, such as IL-1α.

The present invention is based on the finding that ACLF is characterized by hepatocyte GSDMD cleavage, pore formation and release of the pro-inflammatory DAMP IL-1α. Pyroptotic hepatocyte death is a key mechanism in ACLF, and thus pyroptosis itself, and in particular GSDMD, caspase 4, caspase 5 and IL-1α are therapeutic targets in ACLF.

Accordingly, the invention provides an antagonist of the pyroptotic signalling cascade for use in a method of treating or preventing liver failure such as acute liver failure (ALF) and ACLF or for treating an individual suffering from liver failure such as ALF and ACLF.

In particular, the invention provides an antagonist of GSDMD, caspase 4, caspase 5 or IL-1α for use in a method of treating or preventing liver failure such as ALF and ACLF or for treating an individual suffering from liver failure such as ALF and ACLF.

Similarly, the invention provides the use of an antagonist of GSDMD, caspase 4, caspase 5 or IL-1α in the manufacture of a medicament for use in the treatment or prevention of liver failure such as ALF and ACLF or the treatment of an individual suffering from liver failure such as ALF and ACLF.

Similarly, the invention provides a method of treating or preventing liver failure such as ALF and ACLF in an individual in need thereof, said method comprising a step of administering to said individual an antagonist of GSDMD, caspase 4, caspase 5 or IL-1α.

Also the invention provides the use of an antagonist of GSDMD, caspase 4, caspase 5 or IL-1α in the manufacture of a medicament for use in the treatment or prevention of liver failure such as ALF and ACLF or the treatment of an individual suffering from liver failure such as ALF and ACLF.

Similarly, the invention provides a method of treating or preventing liver failure such as ALF and ACLF in an individual in need thereof, said method comprising a step of administering to said individual an antagonist of GSDMD, caspase 4, caspase 5 or IL-1α.

In one particular embodiment, the invention provides an antagonist of GSDMD, caspase 4, caspase 5 or IL-1α as described herein for use in the treatment or prevention of liver failure such as ALF and ACLF.

In addition, the invention provides antagonists of GSDMD, caspase 4, caspase 5 or IL-1α that may be used in the treatment or prevention of aberrant pyroptosis in the kidney, brain, liver or other organ of the body of an individual suffering from a disease or condition characterised by aberrant pyroptosis.

Similarly, the invention provides the use of an antagonist of GSDMD, caspase 4, caspase 5 or IL-1α in the manufacture of a medicament for use in the treatment or prevention of aberrant pyroptosis or the treatment of an individual suffering from aberrant pyroptosis.

Similarly, the invention provides a method of treating or preventing aberrant pyroptosis in an individual in need thereof, said method comprising a step of administering to said individual an antagonist of GSDMD, caspase 4, caspase 5 or IL-1α.

The antagonist for use in accordance with the invention may lead to: (a) decreased expression of GSDMD, caspase 4, caspase 5 or IL-1α in the immune cells and/or peripheral blood and/or liver and/or kidney and/or brain of the individual; and/or (b) decreased levels of GSDMD, caspase 4, caspase 5 or IL-1α in the immune cells and/or peripheral blood and/or liver and/or kidney and/or brain of the individual; and/or (c) decreased activity of GSDMD, caspase 4, caspase 5 or IL-1α in the immune cells and/or peripheral blood and/or liver and/or kidney and/or brain of the individual.

The invention also provides a method of diagnosing liver failure such as ALF and ACLF or predicting the occurrence of liver failure such as ALF and ACLF in a patient and the prognosis of liver failure such as ALF and ACLF in the patient, the method comprising: (a) measuring the level of GSDMD, caspase 4, caspase 5 or IL-1α in the serum or plasma of the patient, and (b) comparing the level of (a) with a known level of GSDMD, caspase 4, caspase 5 or IL-1α from the serum or plasma of a control patient not suffering from liver failure such as ALF and ACLF, wherein an increased level in (a) compared to the control indicates that the patient has liver failure such as ALF and ACLF, that the patient is at increased risk of liver failure such as ALF and ACLF, or defines the severity of liver failure such as ALF and ACLF.

The invention also provides a method of identifying a patient suitable for treatment according to the present invention, the method comprising: (a) measuring the level of GSDMD, caspase 4, caspase 5 or IL-1α in the serum or plasma of the patient, and (b) comparing the level of (a) with a known level of GSDMD, caspase 4, caspase 5 or IL-1α from the serum or plasma of a control patient not suffering from liver failure such as ALF and ACLF, wherein an increased level in (a) compared to the control indicates that the patient may be suitable for treatment according to the present invention. Thus, the patient to be treated in accordance with the present invention may be a patient having an increased level of serum or plasma GSDMD, caspase 4, caspase 5 or IL-1α compared to the level of GSDMD, caspase 4, caspase 5 or IL-1α in the serum or plasma of a control patient, such as a healthy patient, such as a patient not suffering from liver failure such as ALF and ACLF.

The invention also provides a method of identifying an agent suitable for use in treating or preventing liver failure such as ALF and ACLF, the method comprising determining whether a test agent is capable of decreasing the amount or activity of GSDMD, caspase 4, caspase 5 or IL-1α, wherein the ability to decrease the amount or activity of GSDMD, caspase 4, caspase 5 or IL-1α indicates that the compound may be suitable for use in treating liver failure such as ALF and ACLF. In such a method, the amount or activity of GSDMD, caspase 4, caspase 5 or IL-1α may be assessed in the liver or in tissue or cells derived from the liver or other organ of the body. A screening method of the invention may comprise administering the test agent to a bile duct ligated rat or mouse and determining whether the presence of the test agent leads to a decrease in the amount or activity of GSDMD, caspase 4, caspase 5 or IL-1α in the liver of the rat/mouse.

The present invention also provides a method of identifying a patient suitable for treatment of liver failure such as ALF and ACLF, the method comprising:
(a) providing a sample of the serum or plasma of the patient from the subject;
(b) isolating and measuring the level of extracellular vesicles derived from hepatocytes from the sample;
(c) comparing the level of (b) with a known level of extracellular vesicles derived from hepatocytes from the serum or plasma of a control patient not suffering from liver failure such as ALF and ACLF wherein an increased level in (b) compared to the control indicates that the patient may be suitable for treatment of liver failure such as ALF and ACLF.

BRIEF DESCRIPTION OF THE DRAWINGS

FIG. 3—Patient characteristics

(FIG. 4A) Total proteins were extracted from liver tissue from patients with decompensated cirrhosis (DC) (n=7) and ACLF (n=6) and analysed by SDS-PAGE/immunoblotting. Increased cleavage of GSDMD in ACLF is demonstrated by the appearance of the lower molecular weight band corresponding to GSDMD N-terminal fragment. (FIG. 4B) GSDMD cleavage was quantified by densitometry and expressed as ratio of N-terminus/full-length GSDMD. GSDMD cleavage was significantly greater in the ACLF group compared to the control group (Student's t-test; p=0.002).

(FIG. 5A) Mice treated with 20 doses of CCl4 developed advanced fibrosis compared to untreated naïve control (representative Sirius red stain). (FIG. 5B) Intraperitoneal injection of low-dose LPS (2 mg/kg) led to the development of features of ACLF at 4 hours (n=7/group). The CCl$_4$+LPS group demonstrates elevated levels of plasma ALT (left panel, p=0.056), creatinine (centre panel, Student's t-test with Welch correction; p=0.05) and brain swelling (right panel, Student's t-test; p=0.053). (FIG. 5C) Compared to animals treated with CCl$_4$ alone, the CCl$_4$+LPS group show greater cleavage of hepatic GSDMD, expressed as ratio of N-terminus to full-length GSDMD (Student's t-test; p<0.0001). Naïve non-cirrhotic mice, and naïve mice treated with high-dose LPS (12 mg/kg) show no significant increase in hepatic GSDMD cleavage compared to the CCl$_4$ group. Groups not sharing a letter are significantly different (one-way ANOVA with Tukey post hoc test, p<0.01).

(FIG. 6B) GSDMD expression was undetectable by immunoblotting in mouse brain tissue (the right hand lanes show GSDMD in liver extract as positive control).

(FIG. 7A) The enzymatic activity of caspase-11 was measured in whole-liver extracts from snap frozen tissue and was significantly elevated in $CCl_4$-treated mice (n=7) compared to naïve animals (n=5) (Student's t-test; p=0.032). (FIG. 7B) Caspase-11 gene expression was determined from total RNA extracted from snap frozen liver tissue. Expression levels of caspase-11 mRNA were unchanged between the two groups. (FIG. 7C) No changes in the activity of caspase-1 were noted between the $CCl_4$-treated and naïve groups.

(FIG. 8B) Patients with DC showed a higher Caspase-4 enzymatic activity, when compared to non-cirrhotic controls (p=0.013).

(FIG. 9A) Gene expression of the ER-stress marker Ddit3, coding for the protein CHOP, showed a trend towards increase in the $CCl_4$-treated group (Student's t-test; p=0.058) and the abundance of mature CHOP protein was significantly increased in the $CCl_4$-treated group, compared to naïve mice (Student's t-test; p=0.021). (FIG. 9B) The mRNA expression of hepatic Bip was significantly increased in the $CCl_4$-treated group (Student's t-test; p=0.016).

(FIG. 12A) Hepatocyte cell lines treated with LPS from *K. pneumoniae* (100 µg/ml; 4 h) show increased cleavage of GSDMD compared to control [left panel: BNL 1MA.7R.1 cells (Student's t-test; p=0.085); right panel: Huh7 cells (Student's t-test with Welch correction; p=0.065) (n=3 experiments/group)]. (FIG. 12B) LDH release into cell culture medium following LPS exposure was assessed by LDH-Glo assay [left panel: BNL 1MA.7R.1 cells (Student's t-test; p<0.001); right panel: Huh7 cells (Mann Whitney test; p=0.1) (n=3 experiments/group)].

(FIG. 14A) Caspase11$^{-/-}$ mice (right) were treated with 20 doses of CCl4, resulting in a similar level of hepatic fibrosis to wild type (left), as assessed by CPA measurement (n=6/group, Student's t-test; p=0.22). (FIG. 14B) At 4 hours following intraperitoneal LPS injection, mice deficient for caspase-11 (right) displayed significantly lower ALT (Student's t-test; p=0.002), creatinine (Student's t-test; p=0.048), and brain water (Student's t-test; p=0.046) when compared to wild type (left). (FIG. 14C) Hepatocyte cell death was assessed by TUNEL assay, and quantified by measuring positively stained areas. Caspase-11 deficient mice (right) displayed lower levels of hepatocytes cell death than wild type mice (Student's t-test; p=0.051). (FIG. 14D) Lower levels of cell death were reflected also in reduced release of cellular LDH (Student's t-test with Welch correction; p=0.025). (FIG. 14E) No difference was seen between the caspase11$^{-/-}$ (right) and wild type (left) groups in circulating levels of IL-1α, IL-33 or HMGB1. (FIG. 14F) A significant reduction in circulating hepatocyte-derived (ASGPR+) extracellular vesicles was noted in plasma of caspase11$^{-/-}$ mice (right) compared wild type (left) (Mann Whitney test, p=0.006).

DETAILED DESCRIPTION OF THE INVENTION

Figure 1:
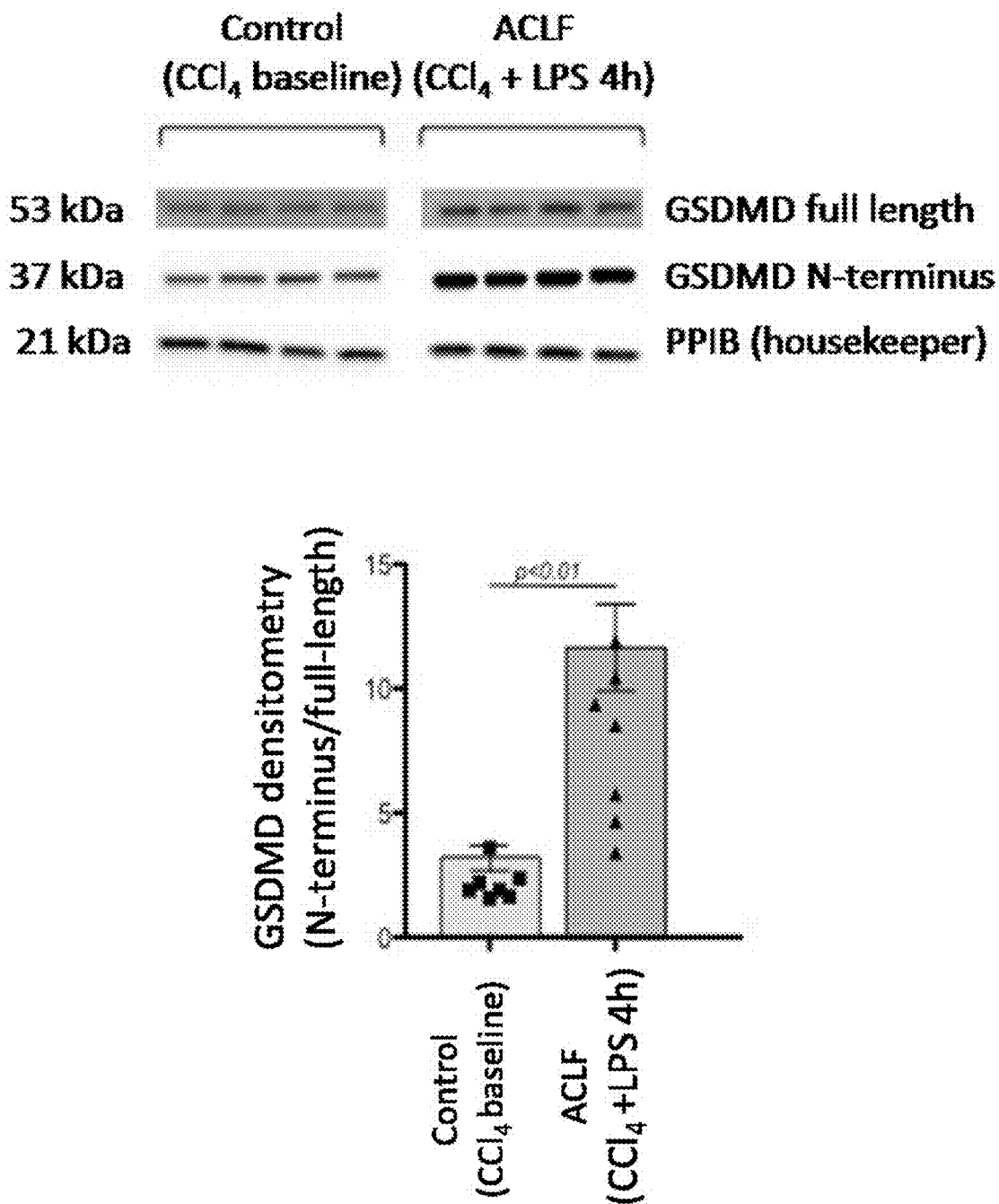
FIG. 1—GSDMD cleavage in liver from control (CCl4 at baseline) and ACLF (CCl4+LPS) mice (N=7/group), presented as representative western blot (left panel) and densitometry of N-terminus: full-length GSDMD (right panel). Bar chart data are mean (SEM). Values compared with unpaired t-test.

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "an antagonist" includes "antagonists", reference to "an antibody" includes two or more such antibodies, and the like.

All publications, patents and patent applications cited herein, whether supra or infra, are hereby incorporated by reference in their entirety.

The inventors have unexpectedly found that ACLF is characterized by hepatocyte GSDMD cleavage, pore formation and release of the pro-inflammatory DAMP IL-1α. They have found that pyroptotic hepatocyte death is a key mechanism in ACLF, and GSDMD, caspase 4, caspase 5 and IL-1α are therapeutic targets in liver failure such as ALF and ACLF.

GSDMD

Gasdermin D (GSDMD) is a member of the gasdermin family. Members of this family appear to play a role in regulation of epithelial proliferation. GSDMD is the effector molecule for the lytic form of cell death called pyroptosis. This process occurs after activation of the inflammasome, a multi-protein complex that recognizes pathogen associated molecular patterns in the cytosol. GSDMD acts by binding to inner membrane lipids, forming pores, and lysing the cells.

Caspase 4/Caspase 5

Caspases comprise a family of aspartate-specific thiol proteases with dimeric structures. Based on sequence homology and functionality, they can be broadly divided into two groups: the apoptotic and the inflammatory caspases. Caspase-5 is part of the latter group which also includes caspase-1 and caspase-4 in humans, and the murine caspase 4/caspase 5 homolog caspase 11.

IL-1α

Interleukin 1 alpha (IL-1α) is one of the members that constitute the IL-1 family of ligands that includes both pro-inflammatory and anti-inflammatory (inhibitory) cytokine species. IL-1α is responsible for the production of inflammation.

The present invention relates to the treatment, prevention and or diagnosis of liver failure such as acute-on-chronic liver failure (ACLF) and/or acute liver failure (ALF).

ACLF

Acute-on-chronic liver failure (ACLF) is a distinct clinical entity encompassing an acute deterioration of liver function in patients with cirrhosis, often decompensated cirrhosis, which is usually associated with a precipitating event and results in the failure of one or more organs and high short term mortality. Unregulated inflammation is thought to be a major contributing factor. A characteristic feature of ACLF is its rapid progression, the requirement for multiple organ supports and a high incidence of short and medium term mortality of 50-90%.

Acute Liver Failure (ALF)

Acute Liver Failure (ALF) is widely accepted as a syndrome of rapid decline in liver function characterized by jaundice, coagulopathy (INR>1.5) and hepatic encephalopathy in patients with no evidence of prior liver disease. Acute liver failure is a further condition where it is thought that non-apoptotic forms of cell death play an important role in disease progression and development, and thus present likely therapeutic targets. There are many causes of ALF including drug toxicity, drug overdose, paracetamol overdose, autoimmune hepatitis, viral hepatitis, Wilson's disease, etc.

Aberrant Pyroptosis

The present invention provides antagonists of GSDMD, caspase 4, caspase 5 or IL-1α that may be used in the treatment or prevention of aberrant pyroptosis in the immune system, kidney, brain, liver or other organ of the body. Aberrant pyroptosis can be considered to be abnormal or pathogenic pyroptosis that occurs as part of a disease or condition. Treating or preventing aberrant pyroptosis by administering antagonists of GSDMD, caspase 4, caspase 5 or IL-1α to individuals in need thereof thus provides treatment of the underlying disease or condition characterised by aberrant pyroptosis. An example of a disease or condition characterised by aberrant pyroptosis is liver failure such as ALF and ACLF.

The present invention thus derives from the inventors' findings of the role of GSDMD, caspase 4, caspase 5 and IL-1α in pyroptosis and ACLF. The present invention utilises these effects by proposing antagonists of GSDMD, caspase 4, caspase 5 or IL-1α as therapeutic agents for use in the treatment or prevention of such conditions.

Antagonists of GSDMD, Caspase 4, Caspase 5 or IL-1α

The present invention relates to the antagonism of GSDMD, caspase 4, caspase 5 or IL-1α. An antagonist of GSDMD, caspase 4, caspase 5 or IL-1α may be any compound or molecule that inhibits or decreases the activity, function or amount of GSDMD, caspase 4, caspase 5 or IL-1α. Preferably the antagonist functions in the immune system and/or liver and/or kidney and/or brain of the patient with liver failure such as ALF and ACLF. The antagonist may act preferentially in the immune system, liver and/or kidney or may act at a number of locations including the immune system, liver and/or kidney and/or brain. Preferably the antagonist leads to a decrease in GSDMD, caspase 4, caspase 5 or IL-1α activity, function or amount in the organs of an individual to whom the antagonist is administered, such as in one of more of the immune system, liver, kidneys, brain, and the heart of the individual. The antagonist may be targeted to the immune system, liver, kidney or other organs such as those listed above during administration as discussed further below.

Preferred antagonists are those that decrease the activity or amount of GSDMD, caspase 4, caspase 5 or IL-1α by at least 10%, at least 20%, at least 30%, at least 40%, at least 50%, at least 60%, at least 70%, at least 80% or at least 90% compared to the amount seen in the absence of the antagonist. For example, decreases of these sizes may be seen in the liver or liver tissue of a subject to whom the agonist has been administered. Decreases of these sizes may be seen in other tissues or organs of the individual, such as in the immune system, brain, kidney and/or heart of the individual.

An antagonist of GSDMD, caspase 4, caspase 5 or IL-1α may reduce the activity or amount of GSDMD, caspase 4, caspase 5 or IL-1α to an amount or activity that is the same, similar to, or equivalent to, that seen in an individual not suffering from ACLF. For example, as explained herein, the expression of GSDMD is increased in association with a model of ACLF. Use of a GSDMD antagonist in accordance with the present invention may lead to a reduction in GSDMD expression in the immune system and/or liver and/or kidneys and/or brain of the individual being treated to a normal level, such as a level that would be seen or would be expected in an individual not suffering from ACLF.

The antagonist may act specifically to antagonise GSDMD, caspase 4, caspase 5 or IL-1α. That is, the effect of the antagonist on GSDMD, caspase 4, caspase 5 or IL-1α may be greater than any other biological effect of the antagonist. Such an antagonist may be specific to the inhibition of GSDMD, caspase 4, caspase 5 or IL-1α, that is it may decrease the activity of GSDMD, caspase 4, caspase 5 or IL-1α, but not other related proteins. Such an antagonist may additionally or alternatively be specific to the expression of GSDMD, caspase 4, caspase 5 or IL-1α, that is it may decrease the expression of GSDMD, caspase 4, caspase 5 or IL-1α but not other related proteins. An antagonist for use in accordance with the present invention may be an antagonist of GSDMD, caspase 4, caspase 5 or IL-1α as described herein, that does not act as an antagonist of other related proteins. An antagonist for use in accordance with the present invention may act on GSDMD, caspase 4, caspase 5 or IL-1α in preference to other related proteins. For example, an antagonist of GSDMD, caspase 4, caspase 5 or IL-1α for use in accordance with the present invention may have one or more of the characteristics of an GSDMD, caspase 4, caspase 5 or IL-1α antagonist as described herein, but may not have such characteristics in relation to other related proteins or may have such characteristics to a lower level in relation to other related proteins when compared to GSDMD, caspase 4, caspase 5 or IL-1α. For example, an antagonist that decreases the activity of GSDMD, caspase 4, caspase 5 or IL-1α may not decrease the activity of other related proteins, or may decrease the activity of other related proteins to a lesser extent, such as a lower percentage decrease, than its effect on GSDMD, caspase 4, caspase 5 or IL-1α. An antagonist that decreases the expression or amount of GSDMD, caspase 4, caspase 5 or IL-1α may not decrease the expression or amount of other related proteins, or may decrease the expression of other related proteins to a lesser extent, such as a lower percentage decrease, than its effect on GSDMD, caspase 4, caspase 5 or IL-1α. An GSDMD, caspase 4, caspase 5 or IL-1α antagonist as described herein may have an effect on other related proteins, such as antagonism of the activity, signalling or expression of one or more other related proteins, that is less than 25%, less than 20%, less than 15%, less than 10%, less than 5%, less than 1%, or less than 0.1% the effect of that antagonist on the activity, signalling or expression of GSDMD, caspase 4, caspase 5 or IL-1α.

By other related proteins it is meant other proteins in the same protein families as GSDMD, caspase 4, caspase 5 or IL-1α. For example, other IL-1 interleukins such as IL-1β can be considered as related proteins of IL-1α. Other members of the gasdermin family can be considered as related proteins of GSDMD. Other inflammatory caspases can be considered as related proteins to caspases 4 or 5.

The specificity of the GSDMD, caspase 4, caspase 5 or IL-1α antagonist may apply within the whole body of the individual to be treated, that is the actions of the GSDMD, caspase 4, caspase 5 or IL-1α antagonist may be specific as discussed above throughout the body of the individual. The specificity of the GSDMD, caspase 4, caspase 5 or IL-1α antagonist may apply within particular tissues of the individual, such as the liver, kidneys and/or heart and/or brain. That is, in one embodiment, the GSDMD, caspase 4, caspase 5 or IL-1α antagonist may act specifically to antagonise GSDMD, caspase 4, caspase 5 or IL-1α as discussed above within the liver and/or kidney and/or other organs of the individual being treated.

The GSDMD, caspase 4, caspase 5 or IL-1α antagonist may therefore be a specific antagonist of GSDMD, caspase 4, caspase 5 or IL-1α as described above. For example, the GSDMD, caspase 4, caspase 5 or IL-1α antagonist may not be an antagonist of other related proteins, or may have no significant effect on the activity or expression of other related proteins.

Any agent capable of inhibiting the activity or function of GSDMD, caspase 4, caspase 5 or IL-1α may be suitable for use in the methods of the present invention. Antagonists for use in accordance with the present invention may be direct or indirect antagonists of GSDMD, caspase 4, caspase 5 or IL-1α.

Indirect antagonists of GSDMD, caspase 4, caspase 5 or IL-1α are agents whose activity is directed to a member of the pyroptotic signalling pathway other than GSDMD, caspase 4, caspase 5 or IL-1α. Inhibition of such members of the pyroptotic signalling pathway act to inhibit pyroptosis, thus indirectly inhibiting the function of GSDMD, caspase 4, caspase 5 or IL-1α.

Direct antagonists are agents whose activity is directly on GSDMD, caspase 4, caspase 5 or IL-1α. For example, direct antagonists may be agents that act directly on GSDMD, caspase 4, caspase 5 or IL-1α to decrease its activity. A direct antagonist may be an agent that disrupts GSDMD, caspase 4, caspase 5 or IL-1α function or that destabilises interaction of GSDMD, caspase 4, caspase 5 or IL-1α with their binding partners. A direct antagonist may decrease the amount of GSDMD, caspase 4, caspase 5 or IL-1α by destroying or disrupting GSDMD, caspase 4, caspase 5 or IL-1α molecules within the patient. A direct antagonist may be an agent that acts on the GSDMD, caspase 4, caspase 5 or IL-1α gene, promoter or other gene regulatory regions to decrease expression of the GSDMD, caspase 4, caspase 5 or IL-1α. A direct antagonist may decrease expression of GSDMD, caspase 4, caspase 5 or IL-1α by preventing or reducing expression from the endogenous GSDMD, caspase 4, caspase 5 or IL-1α gene.

A GSDMD, caspase 4, caspase 5 or IL-1α antagonist may act to disrupt the activity of GSDMD, caspase 4, caspase 5 or IL-1α. For example, the antagonist may act by preventing activation of GSDMD, caspase 4, caspase 5 or IL-1α or by preventing formation of functional complexes comprising GSDMD, caspase 4, caspase 5 or IL-1α.

Any agent or molecule having the properties described above may be used as a GSDMD, caspase 4, caspase 5 or IL-1α antagonist in accordance with the present invention. The test agent may be, or may comprise, for example, a peptide, polypeptide, protein, antibody, polynucleotide, small molecule or other compound that may be designed through rational drug design starting from known antagonists of GSDMD, caspase 4, caspase 5 or IL-1α.

Examples of GSDMD Antagonists

The C-terminus of GSDMD can inhibit N-terminus mediated pyroptosis through structural auto-inhibition. Thus, recombinant C-terminus GSDMD can be used as an inhibitor of GSDMD. The antagonist of GSDMD may be a fragment of GSDMD.

Examples of Caspase Antagonists

Small molecule allosteric site inhibitors of caspase-5 have been identified (Gao and Wells (2012), Identification of Specific Tethered Inhibitors for Caspase-5, Chemical Biology and Drug Design, 79, pages 209-215).

In one embodiment, an antagonist of inflammatory caspases such as caspase-4 may be Disulfiram. Disulfiram has the following chemical formula:

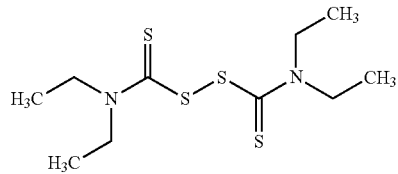 [SMILES: CCN(CC)C(=S)SSC(=S)N(CC)CC]

In another embodiment, an antagonist of inflammatory caspases such as caspase-4 may be Ac-FLTD-CMK (Yang et al. (2018) PNAS 115, 6792-7) or Bay 11-7082 (Hu et al. (2018) bioRxiv 365908). Ac-FLTD-CMK has the formula:

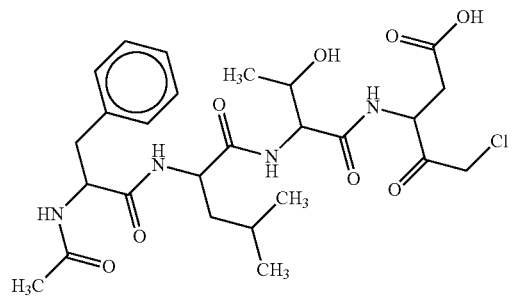

Bay 11-7082 has the formula:

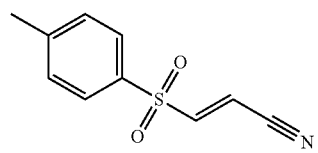

Examples of IL-1α Antagonists

Recombinant or soluble IL-1 receptor 2 (IL1R2) is a negative regulator of IL-1α signalling. Therefore, recombinant IL1R2 infusion is a strategy to limit pyroptosis-driven DAMP signalling in ACLF. In addition, other strategies to increase hepatocellular or circulating IL1R2 levels can be used, including modification of IL1R2 transcription or translation.

Anakinra is a recombinant version of the interleukin 1 receptor antagonist (IL1-RA). Anakinra blocks the biologic activity of naturally occurring IL-1 by competitively inhibiting the binding of IL-1 to the Interleukin-1 type receptor. Rilonacept, also known as IL-1 Trap, is a dimeric fusion protein consisting of the ligand-binding domains of the extracellular portions of the human interleukin-1 receptor component (IL-1R1) and IL-1 receptor accessory protein (IL-1RAcP) linked in-line to the fragment-crystallizable portion (Fc region) of human IgG1. Rilonacept binds and neutralizes IL-1.

The GSDMD, caspase 4, caspase 5 or IL-1α antagonist may be a molecule that is capable of binding to and preventing or disrupting the activity of GSDMD, caspase 4, caspase 5 or IL-1α.

Accordingly, one group of GSDMD, caspase 4, caspase 5 or IL-1α antagonists for use in accordance with this invention are anti-GSDMD, caspase 4, caspase 5 or IL-1α antibodies. Such an antibody may be monoclonal or polyclonal or may be an antigen-binding fragment thereof. For example, an antigen-binding fragment may be or comprise a F(ab)2, Fab, scFv or Fv fragment, i.e. a fragment of the "variable" region of the antibody, which comprises the antigen binding site. An antibody or fragment thereof may be a single chain antibody, a chimeric antibody, a CDR grafted antibody or a humanised antibody.

An antibody may be directed to the GSDMD, caspase 4, caspase 5 or IL-1α molecule, i.e. it may bind to epitopes present on GSDMD, caspase 4, caspase 5 or IL-1α and thus bind selectively and/or specifically to GSDMD, caspase 4, caspase 5 or IL-1α. An antibody may be directed to another molecule that is involved in the expression and/or activity of GSDMD, caspase 4, caspase 5 or IL-1α. For example, a polyclonal antibody may be produced which has a broad spectrum effect against one or more epitopes on GSDMD, caspase 4, caspase 5 or IL-1α and/or one or more other molecules that are involved in the expression and/or activity of GSDMD, caspase 4, caspase 5 or IL-1α.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

An antibody, or other compound, "specifically binds" to a molecule when it binds with preferential or high affinity to the molecule for which it is specific but does substantially bind not bind or binds with only low affinity to other molecules. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

The GSDMD, caspase 4, caspase 5 or IL-1α antagonist may be an antisense oligonucleotide, such as an antisense oligonucleotide against the gene encoding a GSDMD, caspase 4, caspase 5 or IL-1α protein. The term "antisense oligonucleotide" as used herein means a nucleotide sequence that is complementary to the mRNA for a desired gene. Such an antisense oligonucleotide may selectively hybridise with the desired gene. In the context of the present invention, the desired gene may be the gene encoding GSDMD, caspase 4, caspase 5 or IL-1α.

The GSDMD, caspase 4, caspase 5 or IL-1α antagonist may modulate expression of the GSDMD, caspase 4, caspase 5 or IL-1α gene. For example, the GSDMD, caspase 4, caspase 5 or IL-1α antagonist may be a short interfering nucleic acid (siRNA) molecule, double stranded RNA (dsRNA), micro RNA, deoxyribose nucleic acid interference (DNAi) or short hairpin RNA (shRNA) molecule.

The term "selectively hybridise" as used herein refers to the ability of a nucleic acid to bind detectably and specifically to a second nucleic acid. Oligonucleotides selectively hybridise to target nucleic acid strands under hybridisation and wash conditions that minimise appreciable amounts of detectable binding to non-specific nucleic acids. High stringency conditions can be used to achieve selective hybridisation conditions as known in the art. Typically, hybridisation and washing conditions are performed at high stringency according to conventional hybridisation procedures. Washing conditions are typically 1-3×SSC, 0.1-1% SDS, 50-70° C. with a change of wash solution after about 5-30 minutes.

The GSDMD, caspase 4, caspase 5 or IL-1α antagonist may be a nucleic acid molecule such as an antisense molecule or an aptamer. The nucleic acid molecule may bind a specific target molecule.

Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

The terms "nucleic acid molecule" and "polynucleotide" are used interchangeably herein and refer to a polymeric form of nucleotides of any length, either deoxyribonucleotides or ribonucleotides, or analogs thereof. A nucleic acid may comprise conventional bases, sugar residues and internucleotide linkages, but may also comprise modified bases, modified sugar residues or modified linkages. A nucleic acid molecule may be single stranded or double stranded.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by EXonential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579. The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Any of the antagonists described herein may therefore be used to antagonise GSDMD, caspase 4, caspase 5 or IL-1α, i.e. to decrease the amount of GSDMD, caspase 4, caspase 5 or IL-1α that is present, and/or the activity or the function of the GSDMD, caspase 4, caspase 5 or IL-1α. Preferably these antagonising effects take place in the liver and/or kidney and/or brain.

An antagonist of GSDMD, caspase 4, caspase 5 or IL-1α may be an agent that decreases the production of endogenous GSDMD, caspase 4, caspase 5 or IL-1α. For example, the agent may act within the cells of the subject to inhibit or prevent the expression of GSDMD, caspase 4, caspase 5 or IL-1α. Such an agent may be a transcription factor or enhancer that acts on the GSDMD, caspase 4, caspase 5 or IL-1α gene to inhibit or prevent gene expression.

Screening Methods

The present invention also provides methods for the identification of agents suitable for use in the treatment or prevention of liver failure such as ALF and ACLF. For example, the invention provides methods for the identification of antagonists of GSDMD, caspase 4, caspase 5 or IL-1α which are suitable for use in treating liver failure such as ALF and ACLF. Antagonists identified by this method may be antagonists of GSDMD, caspase 4, caspase 5 or IL-1α having any of the characteristics or effects described above. Antagonists identified by the methods described herein may be suitable for use in the treatment or prevention of liver failure such as ALF and ACLF. Antagonists identified by the methods described herein may be suitable for use in the treatment or prevention of aberrant pyroptosis.

Accordingly, the invention provides a method of identifying an agent for use in the treatment or prevention of aberrant pyroptosis or liver failure such as ALF and ACLF, the method comprising determining whether a test agent is capable of decreasing the activity or expression of GSDMD, caspase 4, caspase 5 or IL-1α. For example, the method may involve determining whether a test agent is capable of decreasing the amount or activity of GSDMD, caspase 4, caspase 5 or IL-1α, wherein the ability to decrease the amount or activity of GSDMD, caspase 4, caspase 5 or IL-1α indicates that the compound may be suitable for use in treating or preventing aberrant pyroptosis or liver failure such as ALF and ACLF as described herein.

A test agent for use in a screening method of the invention refers to any compound, molecule or agent that may potentially antagonise GSDMD, caspase 4, caspase 5 or IL-1α. The test agent may be, or may comprise, for example, a peptide, polypeptide, protein, antibody, polynucleotide, small molecule or other compound that may be designed through rational drug design starting from known antagonists of GSDMD, caspase 4, caspase 5 or IL-1α.

The test agent may be any agent having one or more characteristics of an antagonist of GSDMD, caspase 4, caspase 5 or IL-1α as described above.

The test agent to be screened could be derived or synthesised from chemical compositions or man-made compounds. Candidate agents may be obtained from a wide variety of sources including libraries of synthetic or natural compounds. Suitable test agents which can be tested in the above assays include compounds derived from combinatorial libraries, small molecule libraries and natural product libraries, such as display (e.g. phage display) libraries. Multiple test agents may be screened using a method of the invention in order to identify one or more agents having a suitable effect on GSDMD, caspase 4, caspase 5 or IL-1α, such as inhibition of GSDMD, caspase 4, caspase 5 or IL-1α activity or expression.

The screening methods of the invention may be carried out in vivo, ex vivo or in vitro. In particular, the step of contacting a test agent with GSDMD, caspase 4, caspase 5 or IL-1α or with a cell or tissue that comprises GSDMD, caspase 4, caspase 5 or IL-1α may be carried out in vivo, ex vivo or in vitro. The screening methods of the invention may be carried out in a cell-based or a cell-free system. For example, the screening method of the invention may comprise a step of contacting a cell or tissue comprising GSDMD, caspase 4, caspase 5 or IL-1α with a test agent and determining whether the presence of the test agent leads to a decrease in the amount or activity of GSDMD, caspase 4, caspase 5 or IL-1α in the cell or tissue.

For example, the ability of a test agent to decrease the activity or expression of GSDMD, caspase 4, caspase 5 or IL-1α may be tested in a host cell or tissue that expresses GSDMD, caspase 4, caspase 5 or IL-1α. For example, the amount or activity of GSDMD, caspase 4, caspase 5 or IL-1α may be assessed in vitro, in vivo or ex vivo in the liver or in tissue or cells derived from the liver.

In such a cell-based assay, the GSDMD, caspase 4, caspase 5 or IL-1α and/or the test agent may be endogenous to the host cell or tissue, may be introduced into a host cell or tissue, may be introduced into the host cell or tissue by causing or allowing the expression of an expression construct or vector or may be introduced into the host cell or tissue by stimulating or activating expression from an endogenous gene in the cell.

In such a cell-based method, the amount of GSDMD, caspase 4, caspase 5 or IL-1α may be assessed in the presence or absence of a test agent in order to determine whether the agent is altering the amount of GSDMD, caspase 4, caspase 5 or IL-1α in the cell or tissue, such as through regulation of GSDMD, caspase 4, caspase 5 or IL-1α expression in the cell or tissue or through destabilisation of GSDMD, caspase 4, caspase 5 or IL-1α protein within the cell or tissue. The presence of a lower GSDMD, caspase 4, caspase 5 or IL-1α activity or a decreased amount of GSDMD, caspase 4, caspase 5 or IL-1α within the cell or tissue in the presence of the test agent indicates that the test agent may be a suitable antagonist of GSDMD, caspase 4, caspase 5 or IL-1α for use in accordance with the present invention in the treatment of an individual having liver failure such as ALF and ACLF or suffering from aberrant pyroptosis.

In one embodiment, such a cell based assay may be carried out in vitro or ex vivo on cells or tissue deriving from the patient to be treated. It may therefore be determined whether or not the test agent is capable of decreasing the activity or amount of GSDMD, caspase 4, caspase 5 or IL-1α in the cells or tissue of that subject. For example, such a method may be carried out on a sample of cells or tissue from the liver of the patient.

A method of the invention may use a cell-free assay. For example, the GSDMD, caspase 4, caspase 5 or IL-1α may be present in a cell-free environment. A suitable cell-free assay may be carried out in a cell extract. For example, the contacting steps of the methods of the invention may be carried out in extracts obtained from cells that may express, produce or otherwise contain GSDMD, caspase 4, caspase 5 or IL-1α and/or a test agent. A cell-free system comprising GSDMD, caspase 4, caspase 5 or IL-1α may be incubated with the other components of the methods of the invention such a test agent.

In such a cell-free method, the amount of GSDMD, caspase 4, caspase 5 or IL-1α may be assessed in the presence or absence of a test agent in order to determine whether the agent is altering the amount of GSDMD, caspase 4, caspase 5 or IL-1α in the cell or tissue, such as through destabilisation of GSDMD, caspase 4, caspase 5 or IL-1α protein. In either case, the presence of a lower GSDMD, caspase 4, caspase 5 or IL-1α activity or a decreased amount of GSDMD, caspase 4, caspase 5 or IL-1α in the presence of the test agent indicates that the test agent may be a suitable antagonist of GSDMD, caspase 4, caspase 5 or IL-1α for use in accordance with the present invention in the treatment of an individual having liver failure such as ALF and ACLF or suffering from aberrant pyroptosis.

The contacting step(s) of the method of the invention may comprise incubation of the various components. Such incubations may be performed at any suitable temperature, typically between 4° C. and 40° C. Incubation periods may be selected for optimum activity, but may also be optimized to facilitate rapid high-throughput screening. Following the contact and optional incubation steps, the subject methods may further include a washing step to remove unbound components, where such a washing step is generally employed when required to remove label that would give rise to a background signal during detection, such as radioactive or fluorescently labelled non-specifically bound components.

Incubation in cell or cell-free assay systems may be performed in a microtiter plate (e.g. a 96-well plate or other microwell plate). Further, incubation may be performed in an automated fashion (e.g. for high-throughput screening).

A screening method of the invention may be carried out in vivo. For example, a screening method may be carried out in an animal model. In such an in vivo model, the effects of a test agent may be assessed in the liver, or in other organs such as the kidney or heart. Preferably, the animal is a non-human animal such as a rat or a mouse. The screening method of the present invention may comprise the step of administering a test agent to a bile duct ligated rat/mouse or another model of liver failure such as ALF and ACLF such as that caused by administration of carbon tetrachloride and determining whether the presence of the test agent leads to a decrease in the amount or activity of GSDMD, caspase 4, caspase 5 or IL-1α in the immune system, liver, kidney, brain or other organs of the rodent.

Such a model may be used to assess the in vivo effects of a test agent. For example, such a model may be used to assess whether the test agent is capable of decreasing the activity or amount of GSDMD, caspase 4, caspase 5 or IL-1α in vivo. In such a method, the amount of GSDMD, caspase 4, caspase 5 or IL-1α may be assessed and/or the activity of GSDMD, caspase 4, caspase 5 or IL-1α may be assessed.

An in vivo model may also be used to determine whether the test agent has any unwanted side effects. For example, a method of the invention may compare the effects of a test agent on GSDMD, caspase 4, caspase 5 or IL-1α with its effects on other receptors in order to determine whether the test agent is specific.

In an in vivo model as described herein, or an in vitro model such as a cell-based or cell-free assay model as described herein, the effects of a test agent on GSDMD, caspase 4, caspase 5 or IL-1α may be compared with the effects of the same agent on other related proteins. As discussed above, a preferred GSDMD, caspase 4, caspase 5 or IL-1α antagonist for use in a method of treatment as described herein may be an agent that antagonises GSDMD, caspase 4, caspase 5 or IL-1α, but that does not antagonise other related proteins. The screening methods of the invention may thus include an additional step of assessing whether the test agent has any effect on the activity or amount of one or more other related proteins that are not GSDMD, caspase 4, caspase 5 or IL-1α. In such a method, a test agent may be identified as a suitable GSDMD, caspase 4, caspase 5 or IL-1α antagonist if it is found to decrease the activity or amount of GSDMD, caspase 4, caspase 5 or IL-1α, but not to decrease, not to significantly decrease, not to significantly decrease, not to alter, or not to significantly alter, the activity or amount of one or more other related proteins in the same assay.

Where the assay is carried out in vivo, for example in a bile duct ligated rodent (rat/mouse) model or another model of liver failure such as ALF and ACLF such as that caused by administration of carbon tetrachloride as described herein, such a method may comprise comparing the amount or activity of GSDMD, caspase 4, caspase 5 or IL-1α in the immune system, liver, kidney or other organs of the test animal in the presence or absence of the test agent. An observation that the level or activity of GSDMD, caspase 4, caspase 5 or IL-1α is decreased in the immune system, liver, kidney or other organs of animals treated with the test agent suggests that the test agent may be a suitable antagonist of GSDMD, caspase 4, caspase 5 or IL-1α. A further finding that treatment with the same test agent does not significantly decrease or alter the levels or activity of one or more other related proteins, may further indicate that the test agent is a suitable specific antagonist of GSDMD, caspase 4, caspase 5 or IL-1α that may be used in the methods of treatment described herein.

In the screening methods described herein, the presence of a lower GSDMD, caspase 4, caspase 5 or IL-1α activity or a decreased amount of GSDMD, caspase 4, caspase 5 or IL-1α in the presence of the test agent indicates that the test agent may be a suitable antagonist of GSDMD, caspase 4, caspase 5 or IL-1α for use in accordance with the present invention to treat an individual having liver failure such as ALF and ACLF or suffering from aberrant pyroptosis.

A test agent that is an antagonist of GSDMD, caspase 4, caspase 5 or IL-1α may result in a decrease in GSDMD, caspase 4, caspase 5 or IL-1α activity or levels of at least 5%, at least 10%, at least 25%, at least 50%, at least 60%, at least 75%, or at least 85% or more in the presence of the test agent compared to in the absence of the test agent. A test agent that is an antagonist of GSDMD, caspase 4, caspase 5 or IL-1α may result in a decrease in GSDMD, caspase 4, caspase 5 or IL-1α activity or levels such that the activity or level of GSDMD, caspase 4, caspase 5 or IL-1α is no longer detectable in the presence of the test agent. Such a decrease may be seen in the sample being tested or, for example where the method is carried out in an animal model, in particular tissue from the animal such as in the liver.

A test agent that is an antagonist of GSDMD, caspase 4, caspase 5 or IL-1α may be a specific or selective antagonist of GSDMD, caspase 4, caspase 5 or IL-1α as described above. For example, the agent may have an effect on other related proteins, such as antagonism of the activity, signalling or expression of one or more other related proteins, that is less than 25%, less than 20%, less than 15%, less than 10%, less than 5%, less than 1%, or less than 0.1% the effect of that agent on the activity, signalling or expression of GSDMD, caspase 4, caspase 5 or IL-1α.

Levels or amounts of GSDMD, caspase 4, caspase 5 or IL-1α may be measured by assessing expression of the GSDMD, caspase 4, caspase 5 or IL-1α gene. Gene expression may be assessed by looking at mRNA production or levels or at protein production or plasma/serum concentrations. Expression products such as mRNA and proteins may be identified or quantified by methods known in the art. Such methods may utilise hybridisation to specifically identify the mRNA of interest. For example such methods may involve PCR or real-time PCR approaches. Methods to identify or quantify a protein of interest may involve the use of antibodies that bind that protein. For example, such methods may involve western blotting. Regulation of GSDMD, caspase 4, caspase 5 or IL-1α gene expression may be compared in the presence and absence of a test agent. Thus test agents can be identified that decrease GSDMD, caspase 4, caspase 5 or IL-1α gene expression compared to the level seen in the absence of the test agent. Such test agents may be suitable antagonists of GSDMD, caspase 4, caspase 5 or IL-1α in accordance with the invention.

The screening methods may assess the activity of GSDMD, caspase 4, caspase 5 or IL-1α. For example, such a method may be carried out using peripheral blood mononuclear cells. Such cells will produce cytokines such as TNFα and NFkβ on response to stimulation with, for example, lipopolysaccharide (LPS). A screening method may therefore comprise combining peripheral blood mononuclear cells with the test agent or a vehicle and adding LPS. The cells may then be incubated for an amount of time (e.g. 24 hours) to allow the production of inflammatory molecules such as cytokines. The level of cytokines such as TNFα and NFkβ produced by the cells in that time period can then be assessed. If the test agent has anti-GSDMD, caspase 4, caspase 5 or IL-1α properties, then the production of such cytokines or NFkβ should be reduced compared to the vehicle-treated cells.

Pharmaceutical Formulations

A suitable GSDMD, caspase 4, caspase 5 or IL-1α antagonist as described herein is typically formulated for administration with a pharmaceutically acceptable carrier or diluent. The antagonist may be any antagonist as defined herein including any antagonist identified by a screening method of the invention. The antagonist may thus be formulated as a medicament with a standard pharmaceutically acceptable carrier(s) and/or excipient(s) as is routine in the pharmaceutical art. The exact nature of the formulation will depend upon several factors including the desired route of administration. Typically, the antagonist may be formulated for oral, intravenous, intragastric, intravascular or intraperitoneal administration.

The pharmaceutical carrier or diluent may be, for example, an isotonic solution such as physiological saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with ornithine and at least one of phenylacetate and phenylbutyrate, a pharmaceutically acceptable carrier, e.g. sterile water, olive oil, ethyl oleate, glycols, e.g. propylene glycol, and if desired, a suitable amount of lidocaine hydrochloride.

Where the antagonist to be administered is a nucleic acid molecule, for example where the antagonist is in the form of an expression vector, certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules.

A pharmaceutical formulation in accordance with the present invention may further comprise one or more additional therapeutic agents. For example, the formulation may comprise one or more GSDMD, caspase 4, caspase 5 or IL-1α antagonists as defined herein. The formulation may comprise one or more GSDMD, caspase 4, caspase 5 or IL-1α antagonists as described here and also one or more additional therapeutic agents. Preferably the additional therapeutic agent(s) are agents which will assist in the treatment or prophylaxis of the individual to be treated. For example, one or more agents that are effective at treating liver disease may be administered as part of a formulation as described herein. One or more agents that are effective at treating an underlying liver condition or symptom thereof in the patient may be administered as part of a formulation as described herein.

Treatment

The present invention provides methods for the treatment of individuals having liver failure such as ALF and ACLF or suffering from aberrant pyroptosis, particularly for the treatment or prevention of symptoms and conditions associated with or resulting from liver failure such as ALF and ACLF or aberrant pyroptosis.

Accordingly, the invention provides a method of treating an individual having liver failure such as ALF and ACLF comprising administering to said subject an antagonist of the pyroptotic signalling cascade. Similarly, an antagonist of the pyroptotic signalling cascade may be provided for use in a method of treating an individual having liver failure such as ALF and ACLF. Also provided is the use of an antagonist of the pyroptotic signalling cascade in the manufacture of a medicament for use in the treatment of an individual having liver failure such as ALF and ACLF.

Accordingly, the invention provides a method of treating an individual having liver failure such as ALF and ACLF comprising administering to said subject an antagonist of GSDMD, caspase 4, caspase 5 or IL-1α. Similarly, an antagonist of GSDMD, caspase 4, caspase 5 or IL-1α may be provided for use in a method of treating an individual having liver failure such as ALF and ACLF. Also provided is the use of an antagonist of GSDMD, caspase 4, caspase 5 or IL-1α in the manufacture of a medicament for use in the treatment of an individual having liver failure such as ALF and ACLF.

Accordingly, the invention provides a method of treating an individual suffering from aberrant pyroptosis comprising administering to said subject an antagonist of GSDMD, caspase 4, caspase 5 or IL-1α. Similarly, an antagonist of GSDMD, caspase 4, caspase 5 or IL-1α may be provided for use in a method of treating an individual suffering from aberrant pyroptosis. Also provided is the use of an antagonist of GSDMD, caspase 4, caspase 5 or IL-1α in the manufacture of a medicament for use in the treatment of an individual suffering from aberrant pyroptosis.

The antagonist may be any antagonist as described herein including any antagonist identified by a screening method of the invention. The antagonist may be provided in a formulation as described herein. An antagonist of GSDMD, caspase 4, caspase 5 or IL-1α as described herein is thus administered to a subject in order to treat or prevent liver failure such as ALF and ACLF or aberrant pyroptosis, or particular symptoms or conditions associated with liver failure such as ALF and ACLF or aberrant pyroptosis in the subject. An antagonist of GSDMD, caspase 4, caspase 5 or IL-1α as described herein can thus be administered to improve the condition of a subject, for example a subject suffering from liver failure such as ALF and ACLF or aberrant pyroptosis. An antagonist of GSDMD, caspase 4, caspase 5 or IL-1α as described herein may be administered to alleviate the symptoms of a subject, for example the symptoms associated with liver failure such as ALF and ACLF or aberrant pyroptosis.

An antagonist of GSDMD, caspase 4, caspase 5 or IL-1α as described herein may be administered to alleviate the symptoms of a subject, for example the symptoms associated with aberrant pyroptosis.

An antagonist of GSDMD, caspase 4, caspase 5 or IL-1α as described herein may be administered to combat or delay the onset of liver failure such as ALF and ACLF or any symptom associated therewith. The invention can therefore prevent the medical consequences of liver failure such as ALF and ACLF. Use of an antagonist of GSDMD, caspase 4, caspase 5 or IL-1α as described herein may thus extend the life of a patient with liver failure such as ALF and ACLF.

The treatment of liver failure such as ALF and ACLF, refers to the treatment of an individual having or at risk of having liver failure such as ALF and ACLF. The individual may also be suffering from chronic liver disease such as cirrhosis or alcoholic cirrhosis. The patient may be suffering from liver disease or cirrhosis associated with or caused by an infection such as a hepatitis virus infection such as hepatitis C virus infection. The patient may also be suffering from liver disease or cirrhosis associated with or caused by treatment with a hepatotoxin such as acetaminophen (paracetamol). The methods described herein may be used in the treatment of any such disease.

The individual may be suffering from one or more symptoms or conditions caused by or associated with liver failure such as ALF and ACLF. Any one or more of these conditions or symptoms may be treated in accordance with the present invention. For example, the individual may be suffering from, or at risk of, one or more of the following as a result of their liver failure such as ALF and ACLF: renal dysfunction; renal failure; HRS; increased plasma creatinine; brain dysfunction and brain swelling increased plasma ammonia; increased liver enzyme concentrations (such as increased concentrations of ALT and/or AST in the liver); increased inflammation, injury and/or dysfunction in the liver and/or kidney and/or brain and/or blood circulation; liver tissue damage resulting from liver failure, such as resulting from acetaminophen (APAP) toxicity. The individual may be suffering from, or at risk of, acute liver failure, alcoholic hepatitis and/or reperfusion injury of the liver. Those conditions may result from the ALF and/or ACLF of the individual. The methods and uses described herein may be of utility in the treatment or prevention of any one or more of these symptoms or conditions, particularly, in an individual suffering from liver failure such as ALF and ACLF.

In particular, the methods described herein may be used in the treatment of a patient having liver failure such as ALF and ACLF. For example, the patient may have or be at risk or renal failure. The liver failure such as ALF and ACLF may result from an infection and/or inflammation. The liver failure such as ALF and ACLF may result from exposure to a hepatotoxin such as acetaminophen (paracetamol) such as exposure to a high level of the hepatotoxin, such as an overdose with paracetamol. The methods described herein may be used to treat or prevent any of these conditions or symptoms.

As described herein, the antagonist of GSDMD, caspase 4, caspase 5 or IL-1α may lead to decreased expression and/or decreased levels of GSDMD, caspase 4, caspase 5 or IL-1α in the liver of the subject. For example, the antagonist may be an agent that inhibits transcription of GSDMD, caspase 4, caspase 5 or IL-1α in cells of the subject.

As described herein, the antagonist of GSDMD, caspase 4, caspase 5 or IL-1α may lead to decreased activity of GSDMD, caspase 4, caspase 5 or IL-1α in the liver and/or kidney of the individual.

The subject is treated with an antagonist of GSDMD, caspase 4, caspase 5 or IL-1α as described herein. As described above, the antagonist of GSDMD, caspase 4, caspase 5 or IL-1α may be administered alone or in the form of a pharmaceutical formulation. The formulation may comprise one or more antagonists of GSDMD, caspase 4, caspase 5 or IL-1α and may comprise one or more additional therapeutic or prophylactic agents.

Two or more different GSDMD, caspase 4, caspase 5 or IL-1α antagonists as described herein may be used in combination to treat a subject. The two or more antagonists may be administered together, in a single formulation, at the same time, in two or more separate formulations, or separately or sequentially as part of a combined administration regimen.

An antagonist of the invention may be administered in combination with another agents known to be useful in the treatment or prevention of liver failure such as ALF and ACLF. The antagonists may be administered together, in a single formulation, at the same time, in two or more separate formulations, or separately or sequentially as part of a combined administration regimen.

An antagonist or formulation of the invention may be administered by any suitable route. Preferably it is administered by oral, intravenous, intragastric, intraperitoneal or intravascular routes. The antagonist or formulation may be administered directly to the liver of the subject.

The antagonist is administered in a therapeutically effective amount. A suitable dose of an antagonist of the invention can be determined according to various parameters such as the age, weight and condition of the subject to be treated; the type and severity of the liver disease; the route of administration; and the required regimen. A suitable dose can be determined for an individual antagonist. For example, for some antagonists a typical dose may be in the order of from 0.1 mg/kg/day to 30 g/kg/day. A physician will be able to determine the required dosage of antagonist and for any particular subject.

The present invention is broadly applicable to therapeutic methods and is relevant to the development of prophylactic and/or therapeutic treatments. It is to be appreciated that all references herein to treatment include curative, palliative and prophylactic treatment.

Prophylaxis or therapy includes but is not limited to eliciting an effective decrease in GSDMD, caspase 4, caspase 5 or IL-1α amount, function or activity in order to cause a reduction in one or more symptoms or conditions associated with, or resulting from ACLF or aberrant pyroptosis. The symptoms or conditions may be, for example, any of those discussed above. For example, prophylaxis or therapy may result in: reduced symptoms of renal dysfunction, prevention or reduced symptoms of liver failure, reduced levels of plasma creatinine, plasma ammonia, liver enzyme concentrations (such as reduced concentrations of ALT and/or AST in the liver), reduced inflammation in the liver and/or kidney and/or brain and/or blood circulation, and or a reduction in liver tissue damage resulting from liver failure, such as resulting from acetaminophen (APAP) toxicity. Prophylaxis or therapy may result in the maintenance of a particular level of renal dysfunction, renal failure, plasma creatinine, brain dysfunction and/or brain swelling, plasma ammonia, liver enzyme concentrations (such as concentrations of ALT and/or AST in the liver), inflammation in the liver and/or kidney and/or brain and/or blood circulation, and or liver tissue damage resulting from liver failure, such as resulting from acetaminophen (APAP) toxicity, in a patient where such symptoms have been increasing or are expected to increase as a result of the ALF and/or ACLF. Prophylaxis or therapy may result in such changes in symptoms or conditions in such an individual changing at a reduced rate compared to the changes that would have been seen or would have been expected in the absence of such treatment.

Prophylaxis or therapy may have similar effects in relation to any of the symptoms or consequences of liver failure such as ALF and ACLF or aberrant pyroptosis described herein. That is, treatment in accordance with the present invention may lead to a lessening in the severity of such symptoms or consequences, maintenance of an existing level of such symptoms or consequences or a slowing or reduction in the worsening of such symptoms or consequences.

Patients to be Treated

The present invention relates to the treatment or prevention of liver failure such as ALF and ACLF or aberrant pyroptosis in individuals in need thereof. An individual to be treated in accordance with the present invention may therefore have liver failure such as ALF and ACLF or may be at increased risk of liver failure such as ALF and ACLF. For example, the subject may have liver failure. The subject may have immune dysfunction or failure, systemic inflammation, renal failure or brain dysfunction and/or brain swelling.

Methods for diagnosing liver failure, immune dysfunction, renal dysfunction, brain dysfunction, brain swelling or immune failure are well known in the art and in particular to clinicians and veterinarians in the field. For example, renal dysfunction is characterised by a reduction or loss of renal function, which may be assessed by monitoring urine volume, or sodium concentration and osmolality of the urine. Hepatorenal syndrome is also associated with a reduction in renal blood flow. Preferably, the subject will have been diagnosed as having liver failure for example by a medical or veterinarian professional. The subject may display one or more symptoms associated with liver failure, renal dysfunction or renal failure.

Methods for diagnosing liver failure such as ALF and ACLF are well known in the art and in particular to clinicians and veterinarians in the field. ACLF is diagnosed by use of the Chronic Liver Failure (CLiF) Consortium criteria, NACSELD criteria or APASL criteria. Previously validated scores to assess disease severity include Child-Pugh (CP) classification, Model for End Stage Liver Disease (MELD) and the CLiF Consortium Acute Decompensation (CLIF-C AD) score.

The individual to be treated may have increased expression of GSDMD, caspase 4, caspase 5 or IL-1α in the liver compared with a healthy individual, such as an individual not having liver failure such as ALF and ACLF. The individual to be treated may have increased serum or plasma GSDMD compared with a healthy individual, such as an individual not having liver failure such as ALF and ACLF.

A patient may be identified as being suitable for treatment as described herein by a method comprising measuring the level of GSDMD in the serum or plasma of the patient and comparing the level of serum or plasma GSDMD with the level of serum or plasma GSDMD from a healthy individual, such as an individual not having liver failure such as ALF and ACLF. In such a method, an increased level of serum or plasma GSDMD indicates that the patient may be suitable for treatment according to the present invention.

The individual to be treated may have been diagnosed as suffering from liver failure such as ALF and ACLF, or one or more symptoms or conditions as described herein that may be associated with liver failure such as ALF and ACLF, for example by any of these methods. The individual to be treated may have been diagnosed as being at risk of liver failure such as ALF and ACLF. For example, the individual may have been diagnosed with one or more symptoms that are associated with liver failure, cirrhosis, renal failure and/or renal failure. For example, the individual to be treated may have liver cirrhosis, alcoholic hepatitis, idiopathic non-cirrhotic portal hypertension, congenital hepatic fibrosis, partial nodular transformation, Budd-Chiari syndrome, portal vein thrombosis, right heart failure or schistosomiasis infection.

The subject to be treated may be any individual who is susceptible to liver failure such as ALF and ACLF. The subject may be male or female. Women may be more susceptible to the adverse effects of alcohol than men. Women can develop chronic liver disease in a shorter time frame and from smaller amounts of alcohol than men.

The subject to be treated may be a human. The subject to be treated may be a non-human animal. The subject to be treated may be a farm animal for example, a cow or bull, sheep, pig, ox, goat or horse or may be a domestic animal such as a dog or cat. The subject may or may not be an animal model for liver disease. The animal may be any age, but will often be a mature adult subject.

Biomarkers for Diagnosis

As explained above, the present invention relates to the treatment of patients suffering from liver failure such as ALF and ACLF. As reported in the examples, the Inventors have unexpectedly found that there are detectable changes in GSDMD levels in patients and an animal model of liver failure such as ALF and ACLF.

Accordingly, a method is provided for the detection or prediction of liver failure such as ALF and ACLF in an individual as described above. The individual may be any of the individuals as described above under the heading "patients to be treated".

For example, a method of diagnosing liver failure such as ALF and ACLF or of predicting liver failure such as ALF and ACLF in a patient may comprise the steps of (a) detecting the expression or expression pattern of GSDMD, caspase 4, caspase 5 or IL-1α in the serum or plasma of the patient and (b) comparing the expression level or expression pattern of (a) with a control level or pattern of GSDMD, caspase 4, caspase 5 or IL-1α expression based on the expression of GSDMD, caspase 4, caspase 5 or IL-1α found in the serum or plasma of a healthy individual such as an individual not suffering from liver failure such as ALF and ACLF. The method may comprise measuring the level or expression of GSDMD, caspase 4, caspase 5 or IL-1α in the serum or plasma of the patient and in the serum or plasma of a control individual such as a healthy individual described above and comparing the level or expression of GSDMD, caspase 4, caspase 5 or IL-1α in the two samples. The method may comprise measuring the level or expression of GSDMD, caspase 4, caspase 5 or IL-1α in the serum or plasma of the patient and comparing that level with a known control level or expression pattern based on earlier measurements from a control individual or group of control individuals as described above.

For example, a method of diagnosing liver failure such as ALF and ACLF or of predicting liver failure such as ALF and ACLF in a patient may comprise the steps of (a) detecting the expression or expression pattern of GSDMD in the serum or plasma of the patient and (b) comparing the expression level or expression pattern of (a) with a control level or pattern of GSDMD expression based on the expression of GSDMD found in the serum or plasma of a healthy individual such as an individual not suffering from liver failure such as ALF and ACLF. The method may comprise measuring the level or expression of GSDMD in the serum or plasma of the patient and in the serum or plasma of a control individual such as a healthy individual described above and comparing the level or expression of GSDMD in the two samples. The method may comprise measuring the level or expression of GSDMD in the serum or plasma of the patient and comparing that level with a known control level or expression pattern based on earlier measurements from a control individual or group of control individuals as described above.

In such methods, an increased level of GSDMD expression in the serum or plasma of the patient compared with the control level indicates that the patient has an increased likelihood of, an increased risk of or that the individual is already suffering from, liver failure such as ALF and ACLF. An increased level of GSDMD expression in the serum or plasma of the patient compared with the control level indicates that the patient has an increased likelihood of, an increased risk of or that the individual is already suffering from, liver failure such as ALF and ACLF.

Methods are also provided which utilise the findings of the present inventors that serum or plasma GSDMD, caspase 4, caspase 5 or IL-1α levels are increased in liver failure such as ALF and ACLF.

Methods are also provided which utilise the findings of the present inventors that serum or plasma GSDMD levels are increased in liver failure such as ALF and ACLF.

For example, a method of diagnosing liver failure such as ALF and ACLF or of predicting liver failure such as ALF and ACLF in a patient may comprise the steps of (a) measuring the level of GSDMD in the serum or plasma of the patient and (b) comparing the level of (a) with a control level of GSDMD based on the level of GSDMD found in the serum or plasma of a healthy individual such as an individual not suffering from liver failure such as ALF and ACLF. The method may comprise measuring the level of GSDMD in a serum or plasma sample from the patient and in a serum or plasma sample from a control individual such as a healthy individual described above and comparing the levels of GSDMD in the two samples. The method may comprise measuring the level of GSDMD in a serum or plasma sample from the patient and comparing that level with a known control level based on earlier measurements from a control individual or group of control individuals as described above. In such methods, an increased level of serum or plasma GSDMD in the patient compared with the control level indicates that the patient has an increased likelihood of, an increased risk of or that the individual is already suffering from, liver failure such as ALF and ACLF.

A further method may be used to predict whether the patient is likely to suffer from liver failure such as ALF and ACLF. This information may be used by a clinician to determine how the patient is treated and their condition monitored.

Such a method may comprise the steps of (a) measuring the level of GSDMD, caspase 4, caspase 5 or IL-1α in the serum or plasma of the patient and (b) comparing the level of (a) with a known level of GSDMD, caspase 4, caspase 5 or IL-1α based on the level of GSDMD, caspase 4, caspase 5 or IL-1α found in the serum or plasma of a control individual suffering from liver disease who did not go on to suffer from liver failure such as ALF and ACLF. The method may comprise measuring the level of GSDMD, caspase 4, caspase 5 or IL-1α in a serum or plasma sample from the patient and in a serum or plasma sample from the control individual and comparing the levels of GSDMD, caspase 4, caspase 5 or IL-1α in the two samples. The method may comprise measuring the level of GSDMD, caspase 4, caspase 5 or IL-1α in a serum or plasma sample from the patient and comparing that level with a known control level based on earlier measurements from a control individual as described above. In such methods, an increased level of serum or plasma GSDMD, caspase 4, caspase 5 or IL-1α in the patient compared with the control level indicates that the patient has an increased likelihood of, an increased risk of or the individual is already suffering from, liver failure such as ALF and ACLF.

Such a method may comprise the steps of (a) measuring the level of GSDMD in the serum or plasma of the patient and (b) comparing the level of (a) with a known level of GSDMD based on the level of GSDMD found in the serum or plasma of a control individual suffering from liver disease who did not go on to suffer from liver failure such as ALF and ACLF. The method may comprise measuring the level of GSDMD in a serum or plasma sample from the patient and in a serum or plasma sample from the control individual and comparing the levels of GSDMD in the two samples. The method may comprise measuring the level of GSDMD in a serum or plasma sample from the patient and comparing that level with a known control level based on earlier measurements from a control individual as described above. In such methods, an increased level of serum or plasma GSDMD in the patient compared with the control level indicates that the patient has an increased likelihood of, an increased risk of or the individual is already suffering from, liver failure such as ALF and ACLF.

For example, an increased level of serum or plasma GSDMD or of GSDMD expression in these methods when compared with a control level may be a statistically significant increase in serum or plasma GSDMD concentration or GSDMD expression level. An increased level of serum or plasma GSDMD or GSDMD expression in these methods may be an increase of at least 15%, at least 25%, at least 50%, at least 75%, at least 100%, at least 200%, at least 300% or more when compared to a suitable control. The control may be the serum or plasma GSDMD level from a single control individual or may be an average value obtained from a group of control individuals.

The method may comprise testing a sample from the individual for the presence of one or more markers of liver failure such as ALF and ACLF. The presence of such markers in the sample from the individual may indicate that the individual is suffering from liver failure such as ALF and ACLF, or is at increased risk of, liver failure such as ALF and ACLF. The markers may be markers associated with damage to the glomeruli or the renal tubules. For example, if the sample is a sample of serum, the sample may be tested for the presence of one or more markers selected from (a) IL-6 (interleukin-6) and/or IL-10 (interleukin-10) and/or TNFα, (b) MMP-9 (matrix metalloproteinase 9), (c) NAG (N-Acetylglucosamine), (d) myeloperoxidase and (e) glutathione S transferase. Any combination of these markers may be used, optionally with additional markers not specifically mentioned here. Preferably more than one of the markers mentioned above is assessed, such as at least two, at least three, at least four or at least five of these markers.

An individual who has been identified by any such method as having, or being at risk of, liver failure such as ALF and ACLF, may then be provided with appropriate therapeutic or preventative treatment for that condition. This may allow suitable treatment to be provided earlier than would have been possible when detecting liver failure such as ALF and ACLF using known methods. An individual who has been identified by any of these methods as having, or being at risk of, liver failure such as ALF and ACLF, may then be treated by any of the therapeutic or prophylactic methods described herein.

A method may also be provided in order to identify further suitable biomarkers that could be used in the detection methods described herein. This may involve comparing samples obtained from individuals having liver failure such as ALF and ACLF with samples obtained from a normal individual or an individual not having liver failure such as ALF and ACLF. The method may involve identifying markers that can distinguish between a sample from an liver failure such as ALF and ACLF individual and a sample from a normal individual.

A suitable marker may be identified using samples from the organism of interest, such as samples from human individuals. A suitable marker may be identified using samples from an animal model, such as the bile duct ligated (BDL) rat or carbon tetrachloride treated mouse. Such samples may be compared with samples from a normal or sham-treated animal.

The sample may be any suitable sample that can be readily retrieved from a suitable individual, such as a sample of urine, plasma, serum or blood. The marker may be a protein or other molecule that is present in one of the samples, but not in the other sample, or that is present in significantly different amounts in the two samples, such that the samples can be distinguished on the basis of that molecule. A marker that is identified in this way as being capable of distinguishing between the two types of sample may be used in a method as described above in order to determine whether or not an individual, particularly an individual having liver disease, has, or is at risk of, liver failure such as ALF and ACLF. This may be achieved by comparing the presence, absence or amount of the marker in a sample obtained from the individual of interest with the known presence, absence or amount of that marker in known samples, and thereby correlating the sample from the individual with either a control sample from a normal individual or a diseased sample from an individual with liver failure such as ALF and ACLF.

Extracellular Vesicles (EVs)

In some aspects, the biomarker for diagnosing ACLF may also be in the form of an extracellular vesicle.

As used herein, the expression "extracellular vesicles" (EV) refers to subcellular membrane vesicles found in the extracellular environment (e.g., bodily fluids) that originate from cells, and which range in size from about 20 nm to about 1000 nm with a lipid bi-layer membrane. EV may comprise exosomes, microvesicles (MV), multivesicular endosomes (MVE), or vesicles produced by apoptotic bodies, or any combination thereof, as well as other types of extracellular vesicles. Such extracellular vesicles are operable to mediate intercellular communication by either activating surface receptors of recipient cells or by transferring cargo proteins, nucleic acids (DNAs, mRNAs, siRNAs, miRNAs, and small non-coding RNAs), or lipids to recipient cells. One of the most attractive considerations for extracellular vesicles is that a cargo of these extracellular vesicles is protected from extracellular enzymes and an immune system by a lipid membrane bilayer.

Extracellular vesicles may be isolated from many body fluids including blood (plasma and serum), urine, ejaculate, saliva, cerebrospinal fluid, ascites, synovial fluid, bronchoalveolar lavage, pleural effusion, amniotic fluid, sweats, feces, cystic fluids, tears and breast milk. In one embodiment, extracellular vesicles may be isolated from plasma and/or serum.

As such, the methods described herein may comprise obtaining a preparation of isolated extracellular vesicles (EV), and in particular hepatocyte-derived extracellular vesicles from a blood sample of a subject having or suspected of having liver failure such as ALF and ACLF.

In some embodiments, the EVs, in particular hepatocyte-derived EVs comprise vesicles between about 30, 40, 50, 60, 70, 80, 90, or 100 nm to about 500, 600, 700, 800, 900, or 1000 nm in size. In some embodiments, the EVs, in particular hepatocyte-derived EVs comprise vesicles from 100 nm to 1000 nm in size. In some embodiments, the EVs, in particular hepatocyte-derived EVs comprise vesicles between 150 nm to 1000 nm in size. In some embodiments, the EVs, in particular hepatocyte-derived EVs comprise vesicles between 220 nm to 1000 nm in size.

A variety of methods may be used to determine the origin of EV. For example, cell surface markers (e.g., with immunolabeling and/or flow cytometry techniques) may be used to identify, enrich/purify/isolate, and/or quantify EV according to their cell of origin. Of particular interest herein are markers that are present in (or specific for) EV that may be used to identify, enrich/purify/isolate, and/or quantify hepatocyte-derived EV from other types of EV. Examples of such hepatocyte-derived EV markers include AnnexinV and asialoglycoprotein receptor-1 (ASGPR1).

In some embodiments, obtaining a preparation of isolated hepatocyte-derived EVs from a blood sample of a subject (e.g., a subject having or suspected of having Parkinson's disease) may involve identifying, enriching/purifying/isolating, and/or quantifying hepatocyte-derived EVs in a blood sample from the subject. In some embodiments, the blood samples may be processed to obtain platelet-free plasma (PFP), and the preparation of isolated hepatocyte-derived EVs may be prepared from PFP. As used herein, the terms "enriched", "purified", "isolated" and the like, refer to either removing contaminants from a biological sample and/or increasing the concentration of an analyte of interest (e.g., hepatocyte-derived EVs) in the sample, to an extent that is not found in nature. In some embodiments, identifying, enriching/purifying/isolating, and/or quantifying hepatocyte-derived EVs may involve flow cytometry, differential centrifugation, nanomembrane ultrafiltration, immunoabsorbent capture, size-exclusion chromatography, ultracentrifugation, magnetic activated cell sorting (MACS), nanoparticle tracking analysis, light scattering, electrophoretic light scattering, dynamic light scattering, electron microscopy or any combination thereof, or using other techniques that can separate vesicles based on their size and/or surface protein expression. Quantifying hepatocyte-derived EVs may also be performed by methods such as nanoparticle tracking (NTA), biochemical approaches and semi-quantitative electron microscopy approaches. In some embodiments, the methods described herein may further comprise quantifying the level of hepatocyte-derived EVs in a blood sample from a subject. The quantification of hepatocyte-derived EVs may be expressed as a relative value by normalizing the number of hepatocyte-derived EVs (e.g., in terms of the total number of erythrocytes).

In some embodiments, preparations of isolated hepatocyte-derived EVs described herein may comprise at least 70%, 75%, 80%, 85%, 90%, 95%, or 99% (e.g., by weight or number) of hepatocyte-derived EVs, and/or less than 30%, 25%, 20%, 15%, 10%, 5%, or 1% (e.g., by weight or number) of non-hepatocyte-derived EVs.

In some embodiments, an increased level of serum or plasma hepatocyte-derived EVs when compared with a control level may be a statistically significant increase. An increased level of hepatocyte-derived EVs in these methods of the invention may be an increase of at least 15%, at least 25%, at least 50%, at least 75%, at least 100%, at least 200%, at least 300% or more when compared to a suitable control. The control may be the level of serum or plasma hepatocyte-derived EVs from a single control individual or may be an average value obtained from a group of control individuals.

EXAMPLES

Methods

Unless stated otherwise, the Examples were conducted using the following methods.

Patient Characteristics

Patients with end-stage liver disease, listed for liver transplantation, were recruited from Beaujon Hospital, Assistance Publique Hôpitaux de Paris (APHP), Clichy, France, and the Royal Free Hospital, London, United Kingdom. Patients were classified as having decompensated cirrhosis (DC) or ACLF according to the Consortium on Chronic Liver Failure-Sequential Organ Failure Assessment [CLIF-SOFA] classification. Additionally, liver tissue was collected from six participants without fibrosis/cirrhosis at the Royal Free Hospital, London (n=3 hepatic resection for metastatic tumour, n=3 unused donor liver)—these were used as non-cirrhotic controls for some experiments. All liver tissue was prospectively collected at the time of liver resection/transplantation, and snap-frozen in liquid nitrogen.

Mouse Model of Cirrhosis and ACLF

Male C57BL/6j mice, wild type (Charles Rivers, UK) or Casp11$^{-/-}$ (Wang et al. (1998) Cell 92, 501-9), were used for all experiments. Mice were housed in a temperature and light controlled (12 hours light/dark cycle) facility, and received standard chow and water ad libitum.

The model of cirrhosis and ACLF used in this study was as described by Carl et al. (2016) Liver Int 36, 865-73. Briefly, cirrhosis was induced by gavage of carbon tetrachloride ($CCl_4$, 0.5 ml/kg with olive oil vehicle, 20 doses over 10 weeks). Control mice were treated with olive oil alone. Subsequently, low-dose *Klebsiella pneumoniae* lipopolysaccharide (LPS, Merck L4268) was injected intraperitoneally (i.p) at a dose of 2 mg/kg to induce ACLF, or equivalent volume of 0.9% saline as control. For some experiments, a high-dose of LPS (12 mg/kg) was injected in naïve mice. All experiments were terminated at 4 hours following LPS or saline injection.

Histopathological Assessment

Mouse liver sections were fixed, embedded and cut according to standard techniques. Sections were stained with 0.1% Sirius Red (Sigma-Aldrich), and collagen proportionate area (CPA) was calculated by digital image analysis as described in Hall et al. (2013) Histopathology 62, 421-30. Briefly, sections were photographed and red-stained areas of collagen were measured using Zeiss KS300 image analysis software. Additionally, terminal deoxynucleotidyl transferase dUTP nick end labeling (TUNEL) staining was performed on mouse liver sections (In Situ Cell Death Detection Kit, POD—Roche Diagnostics, Burgess Hill, UK) according to manufacturer's protocols. Degree of cell death was quantified by analysis of immunohistochemical positive areas measured by FIJI Image J software as described in Adebayo et al. (2015) Liver Int. 35, 2564-74.

Characterisation of Organ Dysfunction

Mouse plasma alanine aminotransferase (ALT) and creatinine concentration were measured by Cobas Integra 400 automated analyser (Roche Diagnostics, Burgess Hill, UK) using the relevant kits according to the manufacturer's instructions. Plasma lactate dehydrogenase (LDH) was also measured as a circulating marker of non-apoptotic cell death, using the LDHGlo Cytotoxicity Assay (Promega, Chilworth, Hampshire, UK). Brain water was measured according to the technique described in Marmarou et al. (1982) J Neurosurg. 56, 246-53.

Cell Culture

Human (Huh7) and mouse (BNL 1MA.7R.1) hepatocyte cell lines were used for all experiments. These cells were cultured in DMEM with 10% FBS (Life Technologies Ltd., Paisley, UK) according to standard techniques. For some experiments cells were exposed to LPS from *Klebsiella pneumoniae* (Merck, UK), FITC-labelled *E. coli* LPS (Merck, UK), tunicamycin (Merck, UK) or the TLR4 antagonist TAK-242 (Cayman Chemical, USA) according to the doses stated. All measurements were performed in triplicate.

Protein Expression Analysis

Proteins were isolated from snap frozen human and mouse liver samples, and cell culture samples, by standard techniques and analysed by Western blot. Detection was performed using horseradish peroxidase (HRP)-conjugated secondary antibodies (Cell Signalling Technology, Danvers, Mass., USA) and enhanced chemiluminescence (ECL) reagents (BioRad). Densitometric quantification was performed using ChemiDoc imaging stem and Image Lab software (BioRad).

Messenger RNA Expression Analysis

Total RNA was extracted from snap frozen mouse liver and cell samples using standard techniques and gene expression was analyzed according to manufacturer's protocols.

Measurement of Caspase Activity and Damage-Associated Molecular Patterns (DAMPs)

Caspase-1 and Caspase-4/11 activity was measured in human/mouse liver homogenate supernatant using a fluorometric assay as described in Khanova et al. (2018) Hepatology 67, 1737-53. Briefly, Caspase-1 activity was measured by cleavage of the motif WEHD, and Caspase-4/11 by cleavage of the motif LEVD.

A panel of circulating DAMPs were also measured from mouse samples: (i) HMGB-1 was measured from plasma samples by ELISA (Elabscience, USA) according to manufacturer's instructions, (ii) IL-33 was measured from plasma samples by ELISA (Arigo biolaboratories, Taiwan) according to manufacturer's instructions, (iii) IL-1α was measured from serum as follows: briefly, serum samples were incubated with IL-1-sensitive murine cell line EL4, which produces IL-2 upon stimulation with IL-1α. Levels of IL-2 were measured by ELISA (BioLegend, UK), with and without an IL-1α neutralizing antibody (PeproTech EC, UK).

Isolation and Characterization of Extracellular Vesicles

Extracellular vesicles (EVs) were isolated from mouse plasma using a differential centrifugation and ultracentrifugation method as described in Sukriti et al. (2018) Aliment Pharmacol Ther. 47, 1151-61. Briefly, Circulating EVs were isolated from platelet free plasma using differential ultracentrifugation. After isolation the pellet was washed with 1× PBS once and enumerated using flow cytomtery. The spherotech latex size beads of different sizes were used to gate the EVs in range of 0.22-1 µm. The threshold was put on Annexin V+ (BD Biosciences, USA) EVs and ASGPR1 antibody (R&D systems, USA) was used to identify hepatocyte specific EVs. The data was analysed using Flow Jo software (Treestar/BD biosciences, USA).

Statistics

Variables are presented as mean and standard error, or median and interquartile range, depending on normal or non-normal distribution. Data were analyzed by t-test (with Welch correction where necessary), Mann-Whitney test, one-way ANOVA, Chi-Square test or Pearson's correlation as appropriate, using GraphPad Prism (version 5.03 for Windows; GraphPad Software, San Diego, Calif., USA) and Minitab 17 (Minitab, Inc. State College, Pa., USA).

Example 1

Cirrhosis was induced in male C57BL mice by $CCl_4$ gavage (0.5 ml/kg), and ACLF by LPS injection (2 mg/kg i.p). For validation experiments, cirrhosis was induced bile duct ligation (BDL) in Sprague-Dawley rats, and ACLF by LPS injection (0.03 mg/kg i.p). Experiments were terminated at baseline (control) or 4 hours (ACLF) following LPS injection (n=7/group). Plasma ALT, creatinine and brain tissue water content were measured by standard techniques. GSDMD cleavage was assessed by Western blot (ratio cleaved:full-length). IL-1α expression was assessed by immunohistochemistry and ELISA. In vitro experiments were conducted on HepG2 cells, and immunofluorescence was performed using standard techniques.

Data was generated in a mouse model of cirrhosis (CCl4 gavage) with ACLF induced by LPS injection. CCl4+LPS mice show features of ACLF following LPS injection, with increased plasma ALT, creatinine and brain water at 4 hours compared to CCl4 control. A significant increase in cleavage of hepatic GSDMD is seen in CCl4+LPS at 4 hours compared to CCl4 control (FIG. 1).

CCl4+LPS mice show features of ACLF following LPS injection, with increased plasma ALT, creatinine and brain water at 4 hours compared to control. No positive immunostaining for IL-1α was seen at baseline, but following LPS multiple IL-1α positive hepatocytes are visible, consistent with cleavage of pro-IL-1α. A significant increase in hepatic mature IL-1α is noted in the CCL4+LPS group at 4 hours compared to control ($13.7\pm3.5$ vs $3.3\pm0.3$ pg/ml, p<0.05). Importantly, no significant change in hepatic TNF-α or IL-10 was seen. A similar increase in mature IL-1α is seen in BDL+LPS at 4 hours compared to BDL control ($21.7\pm6.9$ vs $0.2\pm0.1$ pg/ml, p<0.01). Cleavage of hepatic GSDMD is seen in CCl4+LPS at 4 hours compared to control (ratio: $7.7\pm1.2$ vs $2.1\pm0.3$, p<0.01). Experiments in HepG2 cells demonstrate exposure to LPS in vitro also leads to GSDMD cleavage. Additionally, immunofluorescence demonstrates cytoplasmic IL-1α expression, which is reduced following LPS, consistent with GSDMD-mediated pore formation and IL-1α release.

Example 2

Figure 2:
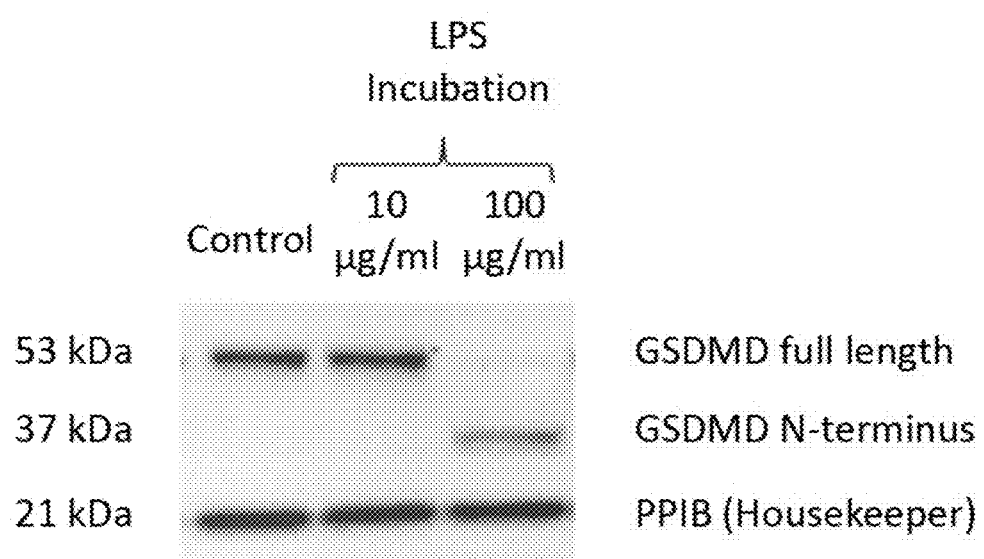
FIG. 2—GSDMD cleavage (left panel) and IL-1α immunofluorescence (IP, right panel) in HepG2 cells exposed to LPS. HepG2 cells demonstrate dose-dependent cleavage of GSDMD in response to LPS incubation for 4 hours (left panel). The same dose and duration of LPS exposure also leads to decreased intracellular IL-1α expression (right panel), consistent with IL-1α release through GSDMD mediated cell membrane pores.
Figure 2:
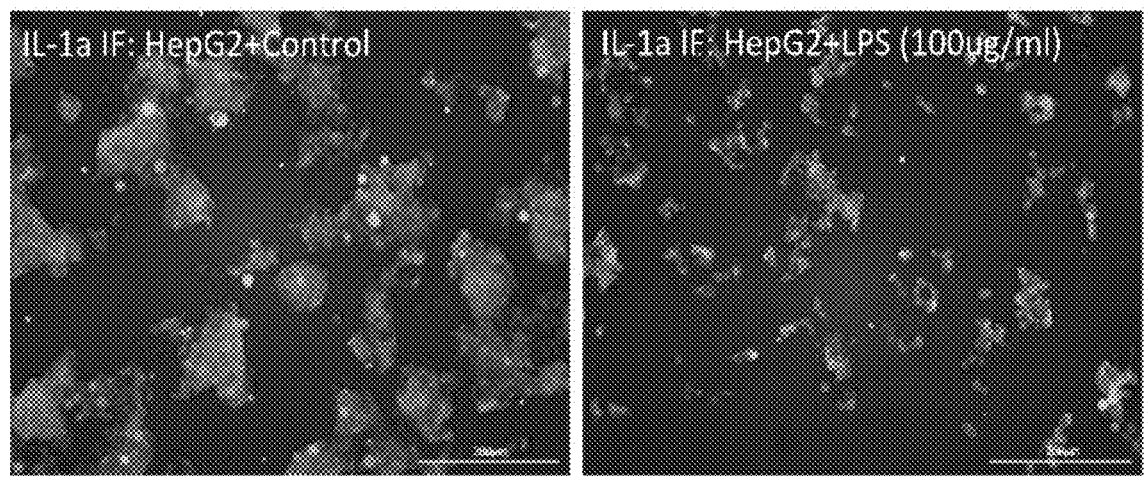

Further studies in hepatocytes have demonstrated that with LPS in vitro leads to dose-dependent cleavage of GSDMD at 4 hours. Over the same time course, immunofluorescence for IL-1α in HepG2 cells demonstrates cytoplasmic expression of pro-IL-1α, which decreases with LPS exposure at 4 hours, consistent with GSDMD-mediated release of mature IL-1α (FIG. 2).

Figure 4A:
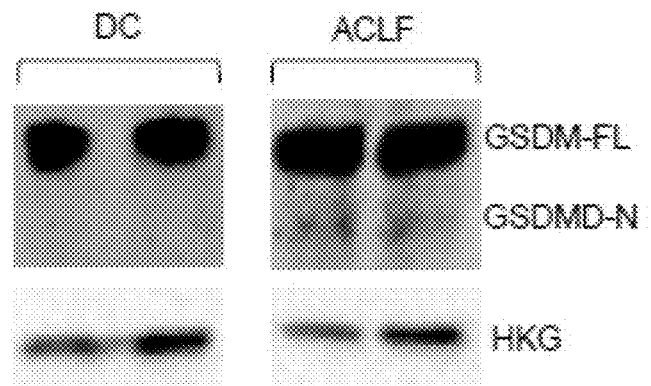
FIGS. 4A-4B—Patients with ACLF display increased cleavage of GSDMD in liver tissue.
Figure 4B:
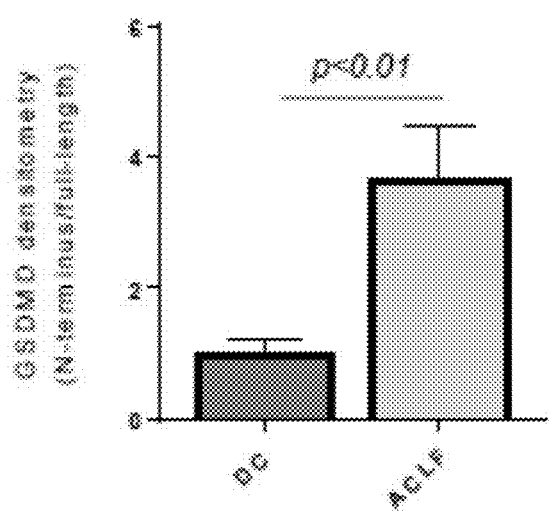

Example 3—GSDMD is Cleaved in Liver Tissue from Patients with ACLF Compared to Patients with Decompensated Cirrhosis Snap frozen explanted liver tissue were collected from 13 patients at the time of transplantation: seven patients with decompensated cirrhosis (DC), and six patients with ACLF (FIG. 3). As seen in the Figure, patients with ACLF had significantly higher values of plasma bilirubin, creatinine, international normalised ratio of prothrombin time (INR), model for end-stage liver disease (MELD) score and CLIF-C ACLF score. Hepatic GSDMD cleavage, as assessed by the ratio of N-terminus to full-length GSDMD level, was significantly greater in the ACLF group compared to DC (FIGS. 4A-4B). Additionally, hepatic GSDMD cleavage was significantly correlated with MELD score (r=0.594, p=0.03) and CLIF-C ACLF score (r=0.595, p=0.03).

Figure 5A:
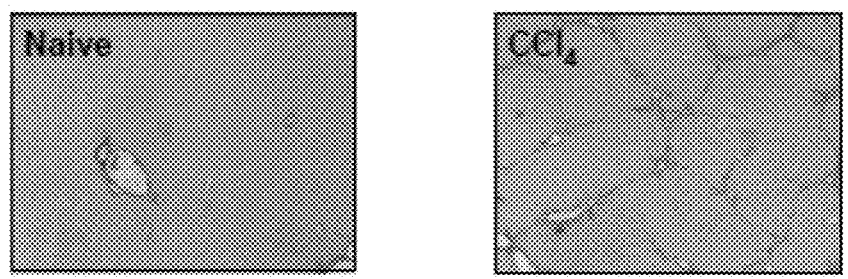
FIGS. 5A-5C—Mouse model of ACLF displays increased cleavage of GSDMD.
Figure 5B:
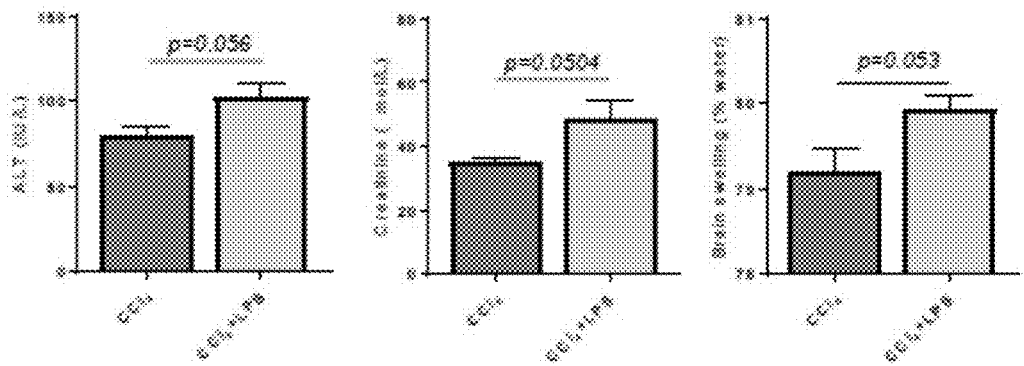
Figure 5C:
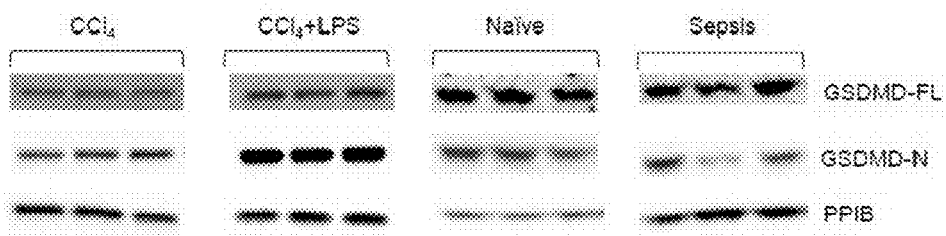
Figure 6A:
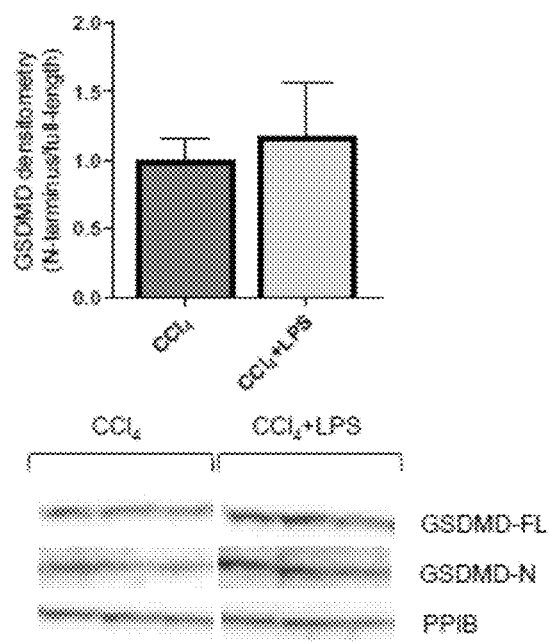
FIGS. 6A-6B—(FIG. 6A) Mice treated with CCl$_4$+LPS do not show increased processing of GSDMD in the kidneys compared to animals treated with CCl$_4$ alone.
Figure 6B:
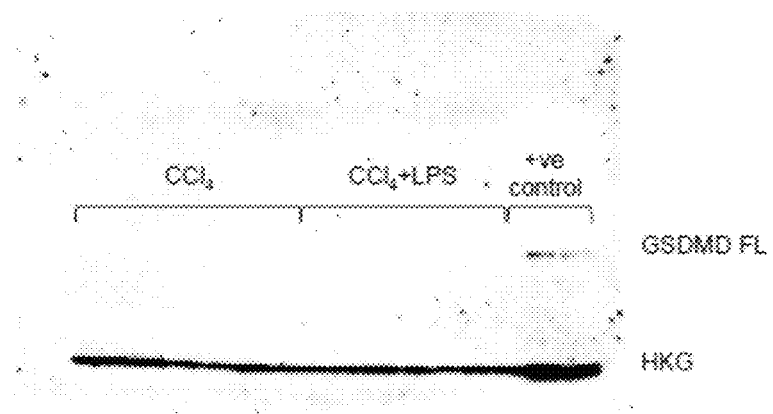

Example 4—Cirrhotic Mice Treated with Low Dose LPS Reproduce Features of ACLF, and Also Demonstrate Hepatic GSDMD Cleavage Mice treated with CCl4 developed advanced fibrosis/cirrhosis compared to naïve controls (FIG. 5A). Following low-dose intraperitoneal (i.p) injection of LPS (2 mg/kg), these mice developed features of ACLF with exaggerated liver injury and extra-hepatic organ injury compared to $CCl_4$ control (FIG. 5B). Similar to the human data above in Example 3, the development of ACLF in this model was associated with increased hepatic GSDMD cleavage in the $CCl_4$+LPS group (FIG. 5C). As further controls, naïve non-cirrhotic mice were treated with high dose LPS (12 mg/kg). In this model, no significant increase in GSDMD cleavage was seen over the baseline level in CCl4-treated mice or naïve non-cirrhotic mice (FIG. 5C). Therefore, $CCl_4$-treated cirrhotic mice demonstrate enhanced sensitivity to hepatic GSDMD cleavage following LPS exposure, compared to naïve mice. Importantly, no increase in GSDMD cleavage was seen in the kidneys, and no GSDMD expression at all in brain, of the $CCl_4$+LPS group compared to $CCl_4$ alone despite the increase in plasma creatinine and brain water noted in the $CCl_4$+LPS group (FIGS. 6A-6B).

Figure 7A:
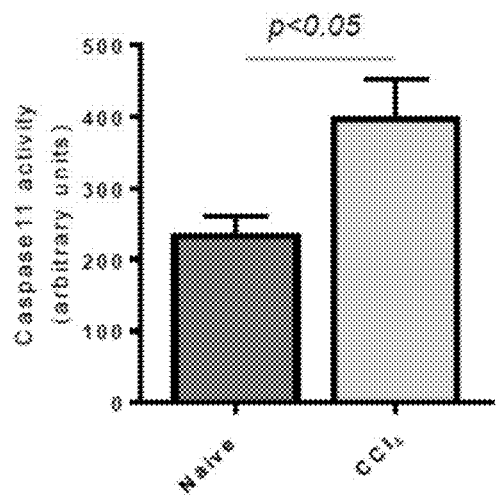
FIGS. 7A-7C—Hepatic caspase-11 activity is increased in cirrhotic mice.
Figure 7B:
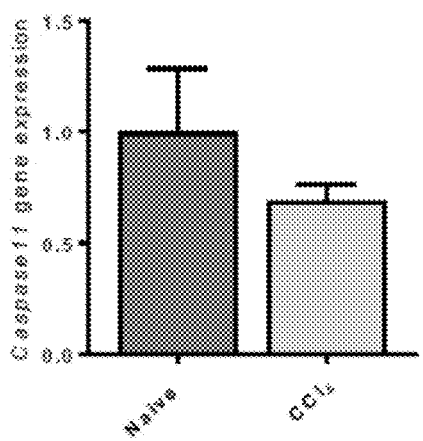
Figure 7C:
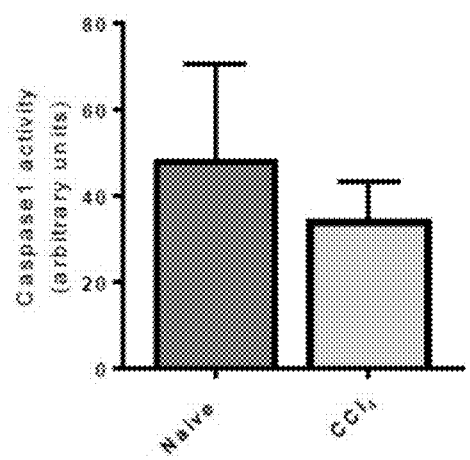

Example 5—Liver Tissue from Humans and Mice with Cirrhosis Demonstrate Increased Caspase-4/11 Activity Compared to Non-Cirrhotic Controls Hepatic caspase-1 and caspase-11 activity was measured in naïve and $CCl_4$-treated mice. This demonstrated no change in caspase-1 activity, but a significant upregulation in caspase-11 activity in $CCl_4$-treated mice compared with control (FIG. 7A). A similar effect was seen for caspase-4 activity in human liver samples from patients with cirrhosis compared to noncirrhotic control samples (FIG. 7C). These findings are consistent with increased activity, or 'sensitisation', of the non-canonical inflammasome in liver tissue in cirrhosis.

Figure 8A:
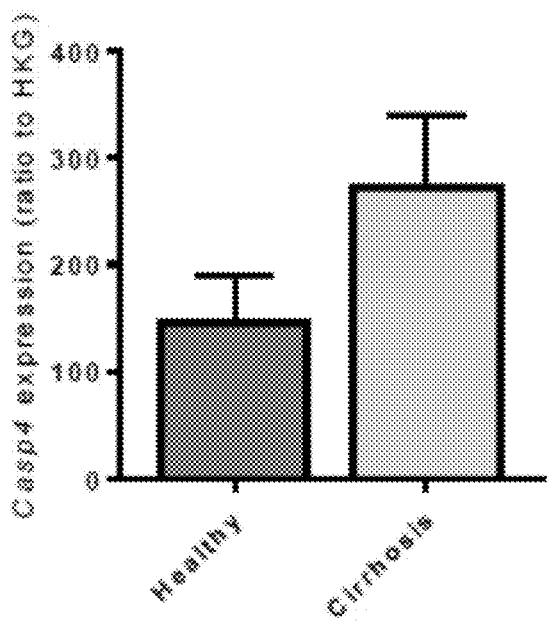
FIGS. 8A-8B—(FIG. 8A) The gene expression of Caspase-4 in patients with decompensated cirrhosis (DC, n=12) was not significantly different from non-cirrhotic controls (n=9) (Student's t-test; p=0.152).
Figure 8B:
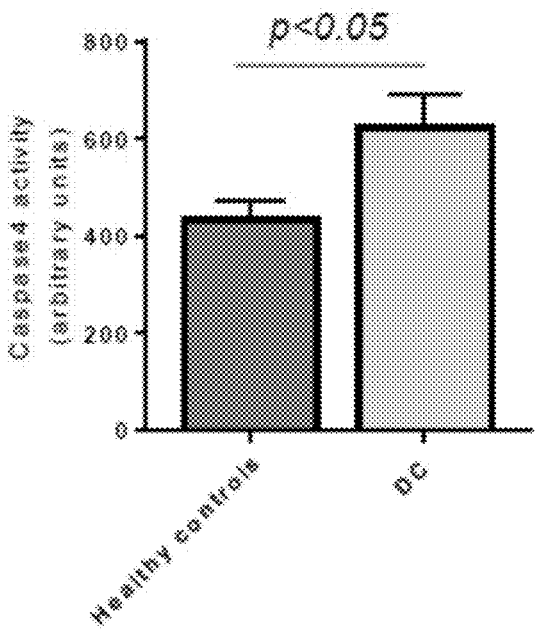
Figure 9A:
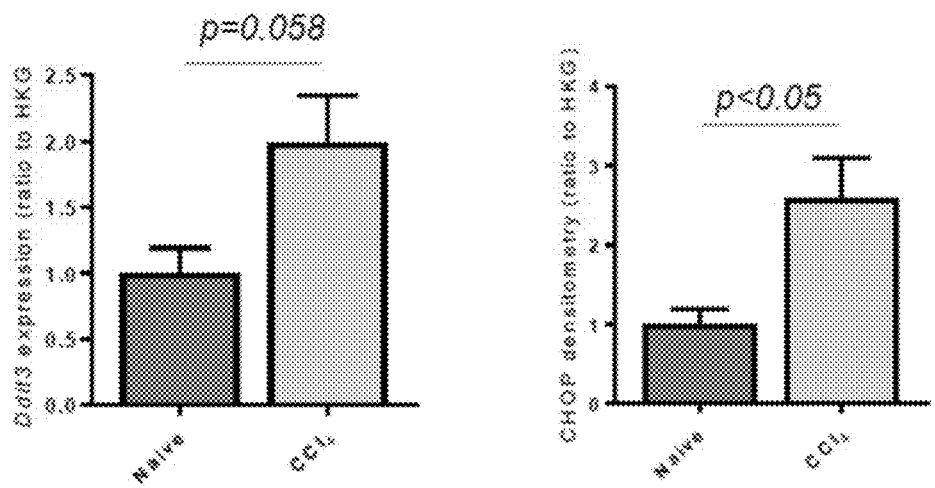
FIGS. 9A-9B—Cirrhotic mice demonstrate increased hepatic endoplasmic reticulum stress. Gene and protein expression of key genes was measured by real-time qPCR and/or SDS-PAGE/immunoblotting from snap frozen whole-liver tissue in $CCl_4$-treated (n=7), and naïve (n=5) mice.
Figure 9A:
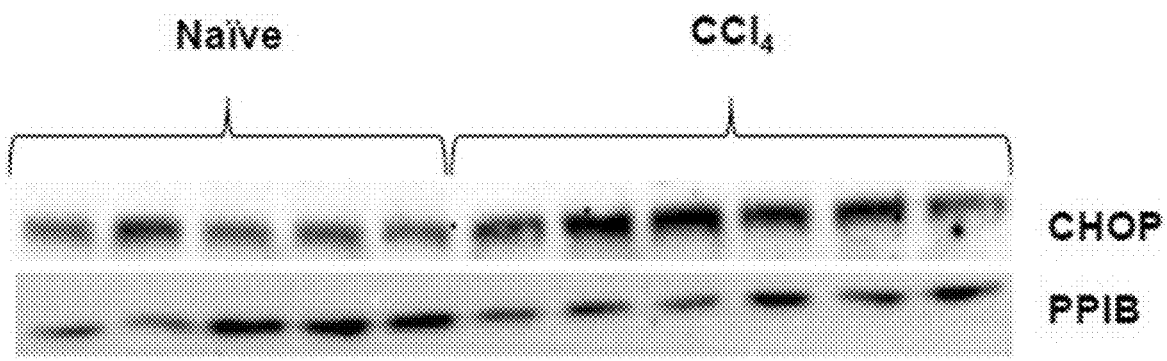
Figure 9B:
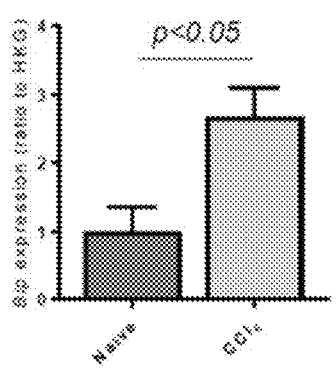

Example 6—Endoplasmic Reticulum Stress is Associated with the Upregulation in Caspase-11 Activity in Cirrhosis The expression of liver caspase-11 mRNA from mouse samples, and liver caspase-4 mRNA from human samples, was measured. Although a trend towards increased levels was seen in the cirrhotic samples, these differences did not attain statistical significance (FIG. 7B and FIGS. 8A-8B). It is known that endoplasmic reticulum (ER) stress is associated with liver fibrosis and cell death. ER stress occurs as a consequence of disrupted intracellular homeostasis and an accumulation of misfolded proteins. ER stress has also been associated with induction of caspase-11 activity, through a direct interaction with the ER stress protein C/EBP homologous protein (CHOP). Accordingly, CHOP protein expression was measured in liver tissue from naïve and cirrhotic mice, and a significant upregulation of CHOP mRNA and protein expression was found in cirrhotic mice compared to control (FIG. 9A). Additionally, increased levels of other markers of ER stress were found in $CCl_4$-treated mouse liver: significantly increased mRNA expression of the ER chaperone protein GRP78 and a trend towards increased mRNA expression of X-box binding protein 1 (splice variant sXBP1) (FIG. 9B). These results demonstrate an association of hepatic ER stress with upregulation of the caspase-11 pathway in $CCl_4$-treated mice.

Figure 10:
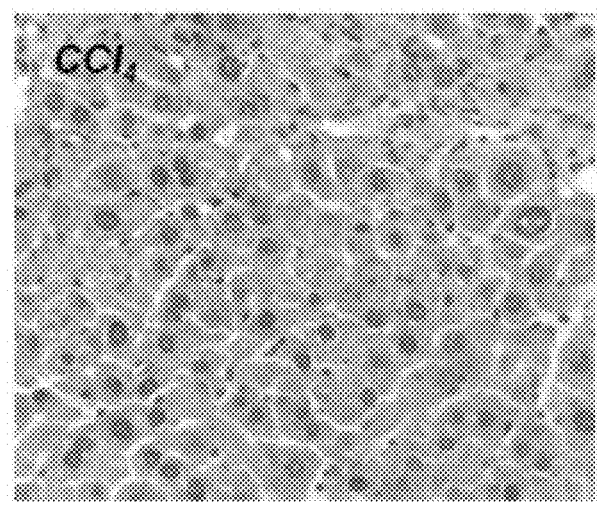
FIG. 10—Hepatocyte cell death in mice treated with $CCl_4$+LPS was assessed by TUNEL assay. Quantification of the % area positive for the staining was showed increased cell death compared with mice treated with $CCl_4$ alone (Mann Whitney test; p=0.014).
Figure 10:
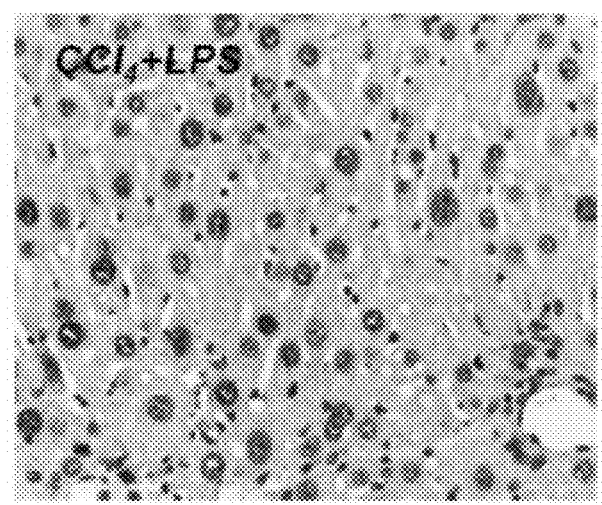
Figure 10:
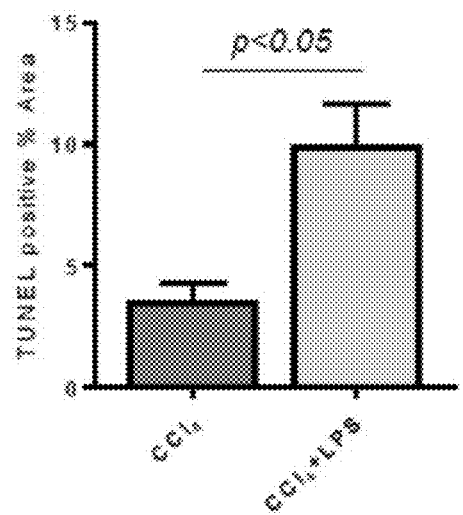

Example 7—Hepatocytes Undergo Pyroptosis in a Dose-Dependent Manner in Response to LPS, and are 'Sensitized' by Prior Low-Dose LPS Exposure and ER Stress TUNEL staining of liver tissue from CCl4 and CCl4+LPS mice confirmed that hepatocytes are the key cells undergoing apoptotic and non-apoptotic cell death in rodent models of ACLF14, which demonstrated primarily hepatocyte death following LPS injection, and a significant increase in overall cell death in the $CCl_4$+LPS group (FIG. 10).

Figure 11:
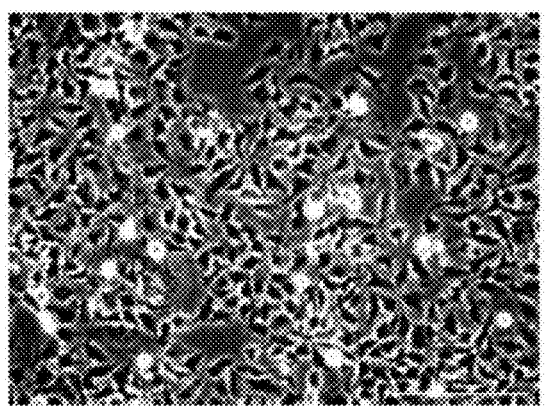
FIG. 11—Huh7 cells uptake FITC-labelled LPS at 3 h hrs, compared to negative control, as shown by the presence of intracellular fluorescent inclusions (red arrows).
Figure 11:
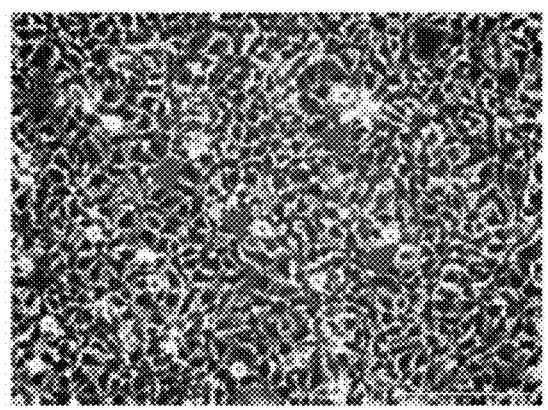

It is also known that hepatocytes can actively internalize LPS through carrier mechanisms, and that hepatocytes play a key role in the clearance of LPS during endotoxaemia. This observation was confirmed in human hepatocytes (Huh7), with co-incubation with FITC-labelled LPS demonstrating active internalization of LPS within 4 hours (FIG. 11).

Figure 12A:
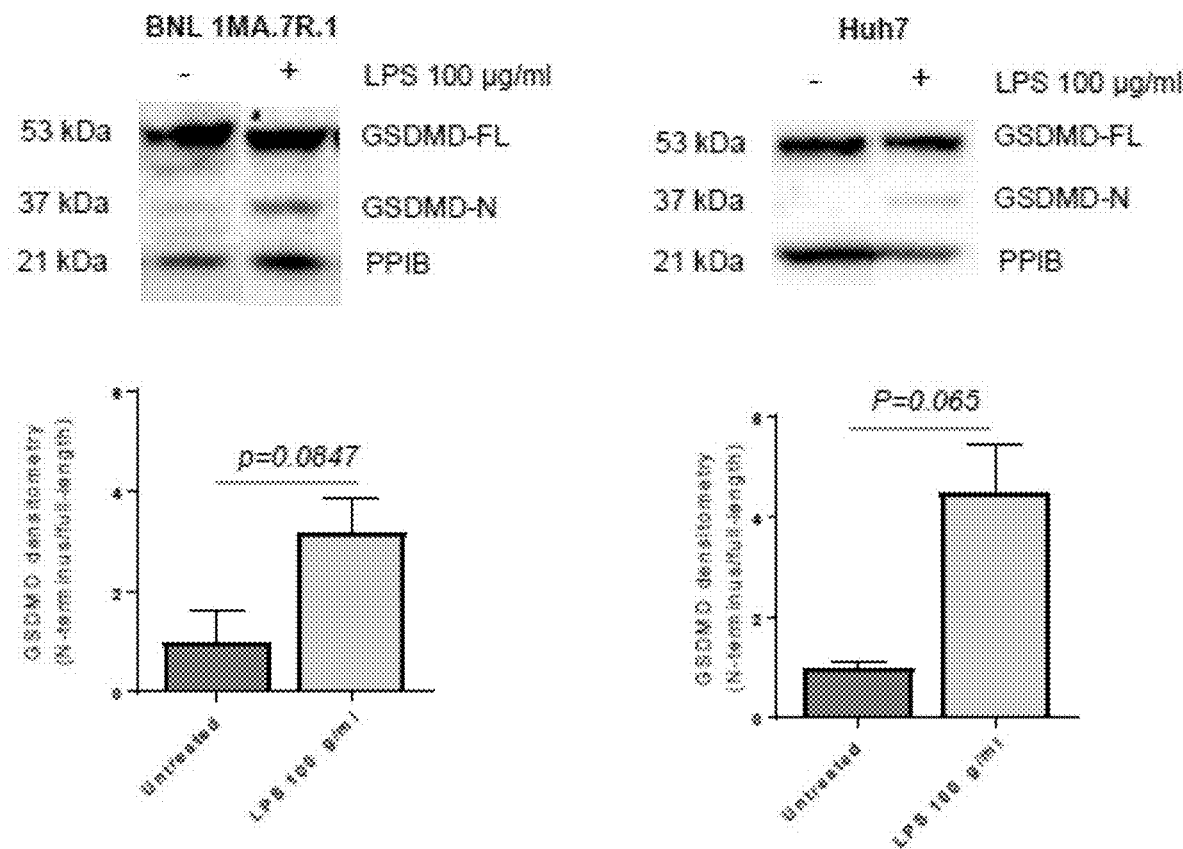
FIGS. 12A-12B—LPS-dependent pyroptosis in hepatocytes and priming by ER stress.
Figure 12B:
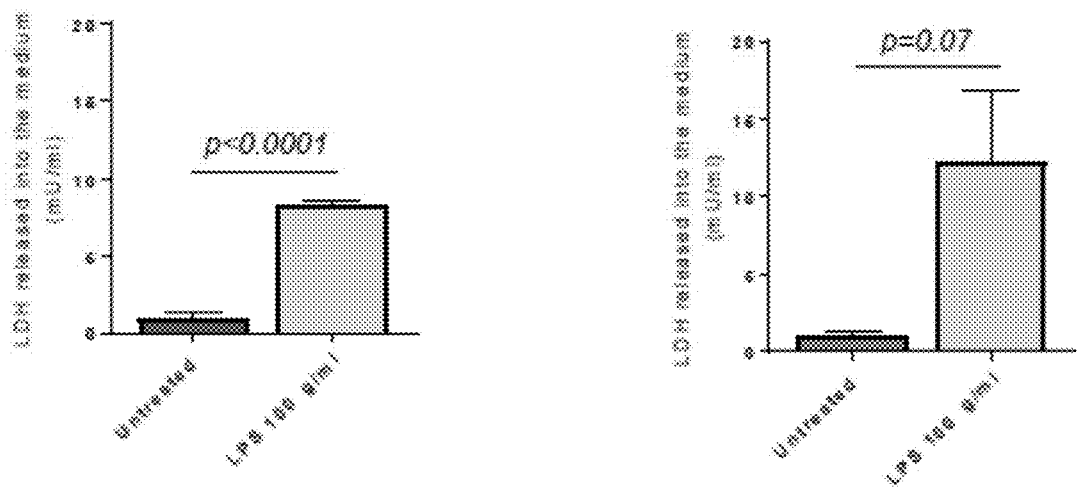

To determine if hepatocytes undergo pyroptosis in response to LPS exposure, human (Huh7) and mouse (BNL) hepatocytes were exposed to LPS (100 μg/ml) in vitro, which led to dose dependent GSDMD cleavage and LDH release within 4 hours (FIGS. 12A-12B).

Figure 13:
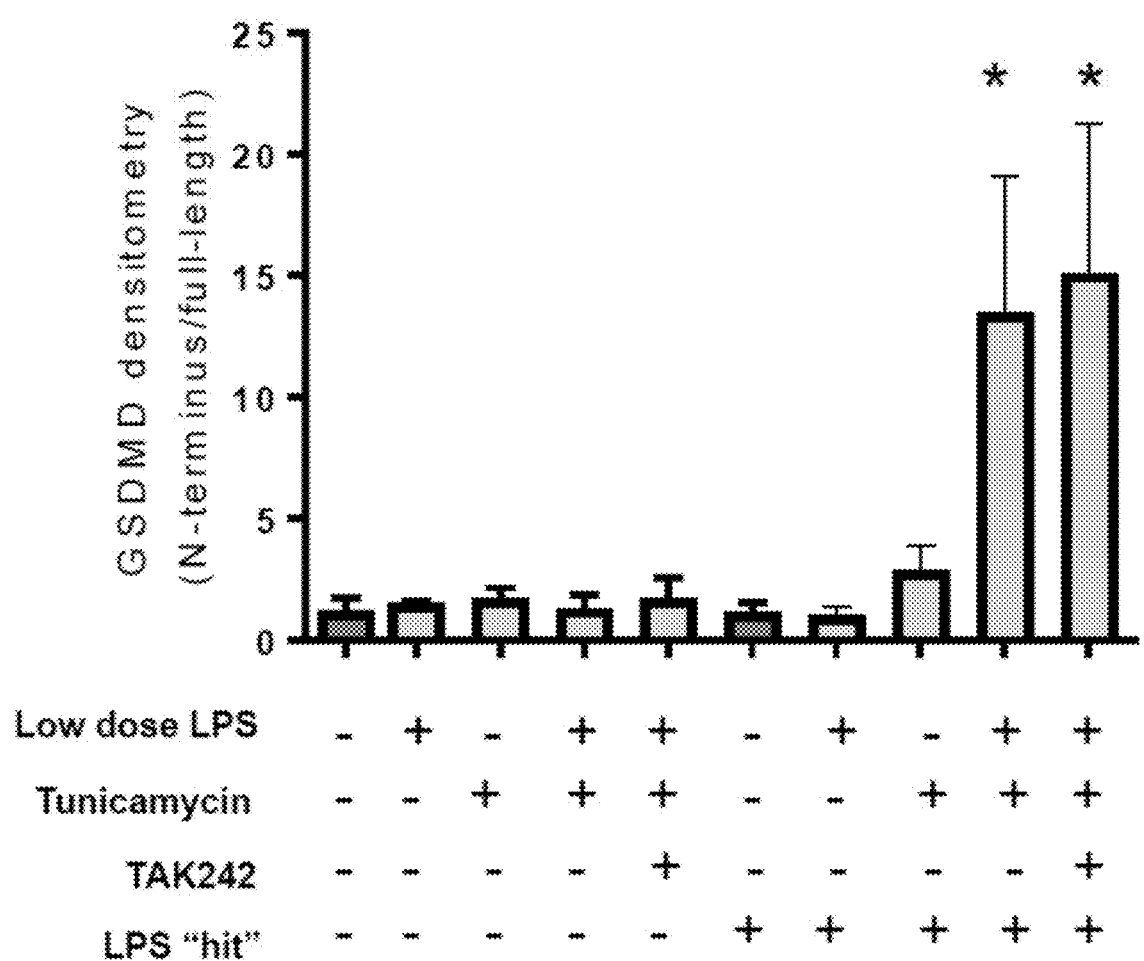
FIG. 13—LPS-dependent pyroptosis in hepatocytes and priming by ER stress. Huh7 primed for 24 h with low-dose LPS and the ER-stress inducer tunicamycin showed increased susceptibility to LPS treatment (30 µg/ml; 4 h) compared to cells exposed to LPS without priming or primed with LPS or tunicamycin alone (one-way ANOVA with Tukey post hoc test, p<0.01).
Figure 14A:
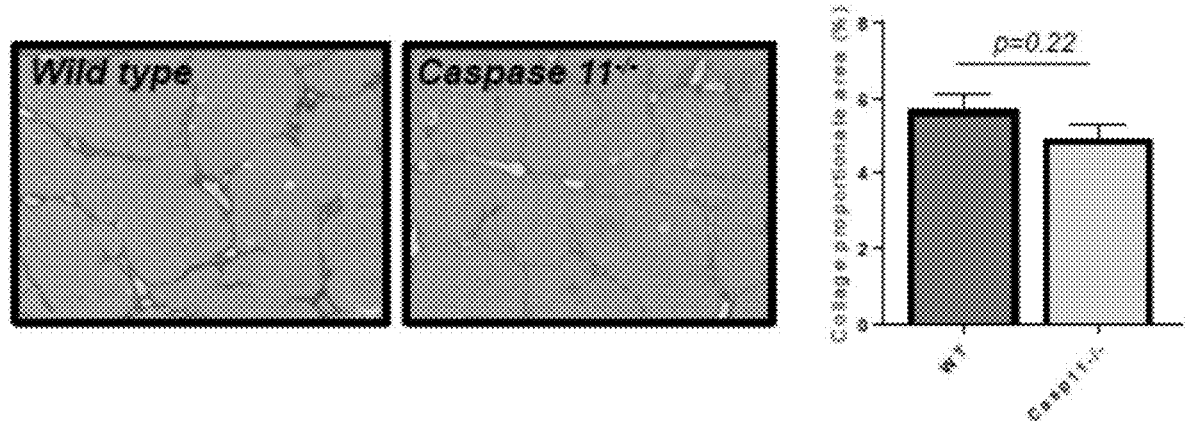
FIGS. 14A-14F—Caspase-11 deficiency protects from hepatic and extra-hepatic organ injury in ACLF.
Figure 14B:
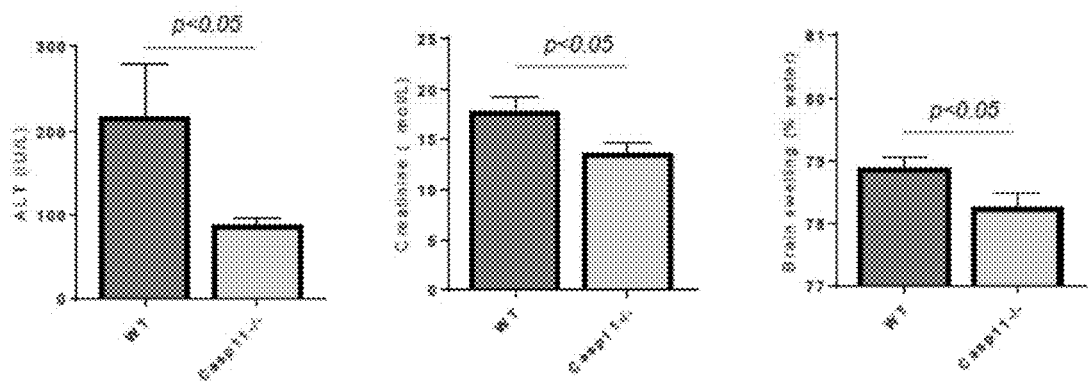
Figure 14C:
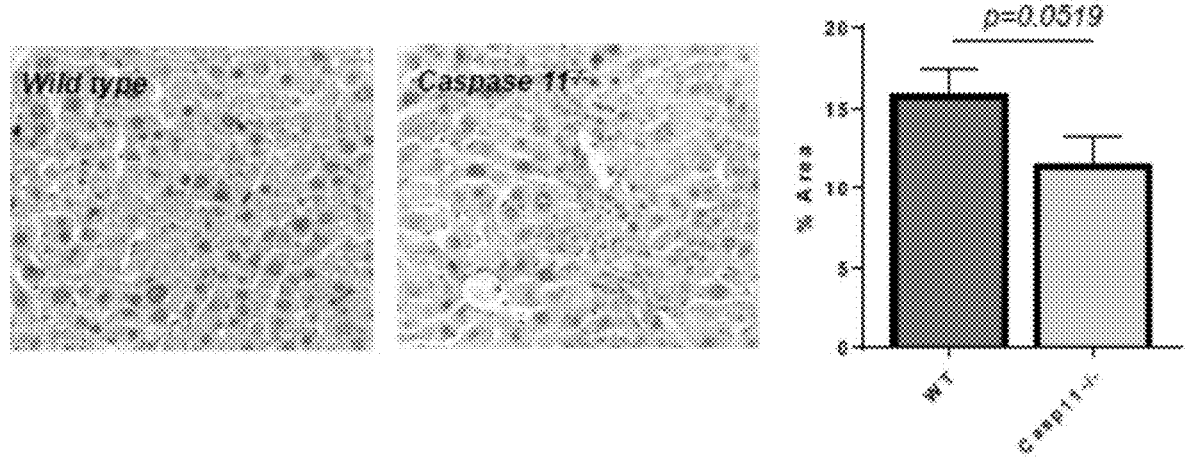
Figure 14D:
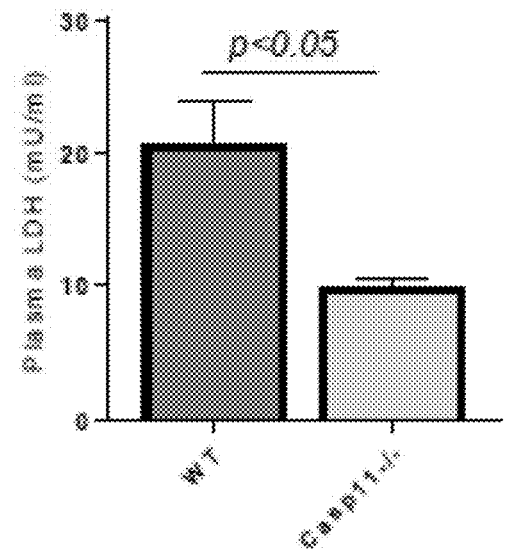

In addition to hepatocyte ER stress, increased levels of circulating endotoxin are detected in advanced liver disease. Therefore, to determine the importance of hepatocyte ER stress and low-level endotoxin exposure as mediators of upregulation of the caspase-4/11 pathway, Huh7 hepatocytes were pre-treated with the ER stress inducer, tunicamycin and/or very low-dose LPS (1 μg/ml) for 24 hours, prior to the LPS 'hit' (30 μg/ml) (FIG. 13). These experiments demonstrated a marked increase in sensitivity to LPS-induced pyroptosis in hepatocytes pre-treated with tunicamycin and very low-dose LPS. Importantly, in these experiments hepatocyte pyroptosis was independent of the TLR4 pathway, as GSDMD cleavage was not inhibited by the TLR4 antagonist TAK-242. Caspase-11 deficient mice are protected from hepatic and extra-hepatic organ injury in ACLF $Casp11^{-/-}$ mice are deficient in the caspase-11 pathway, but the caspase-1 pathway remains intact. $Casp11^{-/-}$ mice develop a similar level of advanced fibrosis/cirrhosis compared to wildtype (wt) after treatment with 20 doses of $CCl_4$ (FIG. 14A). However, following injection with low dose LPS, these mice demonstrated significant protection from hepatic and extrahepatic organ injury (FIG. 14B). This was associated with a significant reduction in circulating LDH, and in TUNEL-positive cells on liver immunostaining, suggesting a reduction in hepatocyte cell death (FIGS. 14C-14D).

Figure 14E:
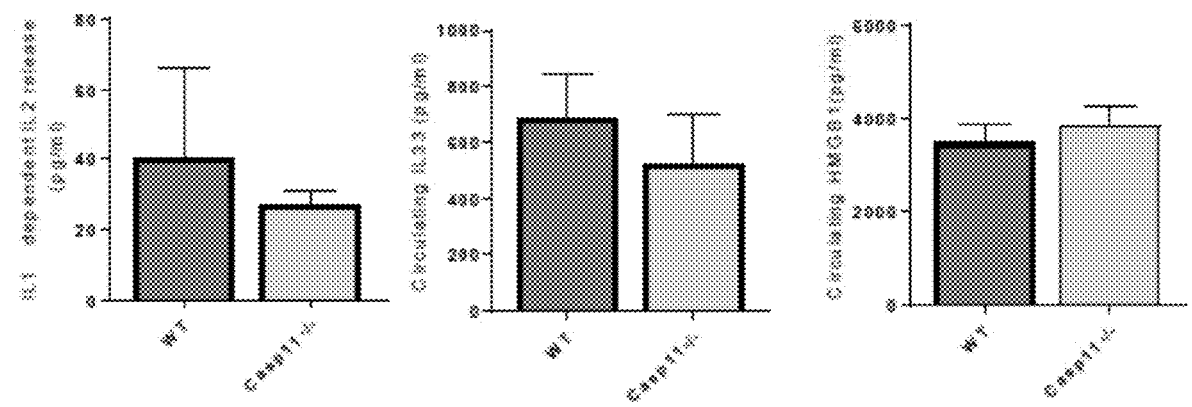

To further explore the mechanism of protection of the extra-hepatic organs in $Casp11^{-/-}$ mice, a panel of circulating DAMPs were measured as potential products of hepatocyte cell death that may be involved in inter-organ signalling. A trend towards reduction in IL-33 was noted in $Casp11^{-/-}$ when compared to wild type (FIG. 14E).

Figure 14F:
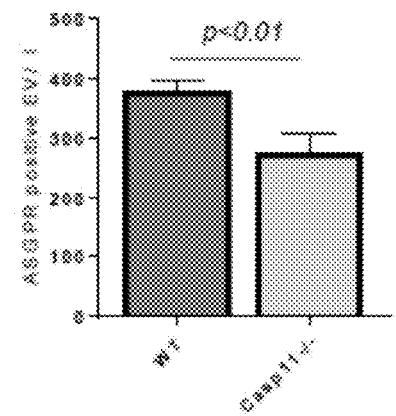

Since EVs have been shown to mediate interorgan communication, hepatocyte-derived EVs were measured in wild type and $Casp11^{-/-}$ mice treated with $CCl_4$+LPS. This demonstrated a significant reduction in circulating hepatocyte derived EVs in $Casp11^{-/-}$ when compared to wild type (FIG. 14F). This suggests that cell death by pyroptosis results in the release of EVs which may further perpetuate the inflammatory cascade in tissue.

Example 8—Disulfiram Inhibits Pyroptosis

Figure 15:
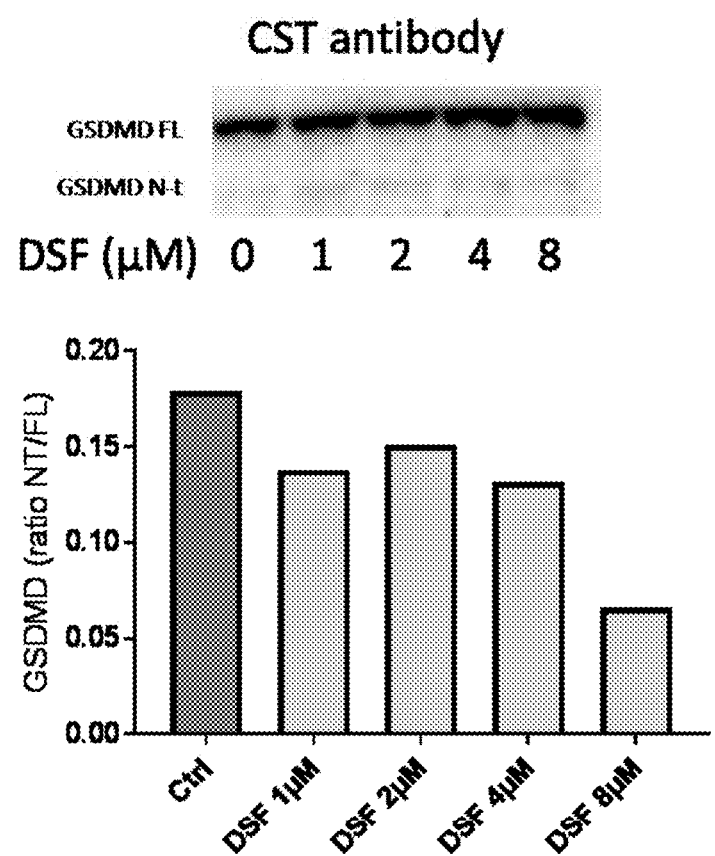
FIG. 15—Immunoblotting analysis of HUH7 cellular proteins after incubation with disulfiram and LPS. GSDMD was detected in two forms—the N-terminal form (N-t) and the full-length (FL) form, and their ratios calculated.

HUH7 were cultured in a 6-well plate to 70-80% confluency. Culture medium (DMEM+10% FBS) was removed and cells incubated with 0, 1, 2, 4 or 804 of Disulfiram (DSF) for 1 hour in serum-free DMEM before adding LPS from *K. pneumoniae* (85 μg/ml) to each well. Total proteins were extracted after 2 hours and analysed via immunoblotting. The results are shown in FIG. 15. This shows that a higher dose of Disulfiram results in a decreased ratio of N-terminal GSDMD to full-length GSDMD.

CONCLUSIONS

This study demonstrates, for the first time, that ACLF is characterized by hepatocyte GSDMD cleavage, pore formation and release of the pro-inflammatory DAMP IL-1α. These findings suggest pyroptotic hepatocyte death as a key mechanism in ACLF, and support GSDMD and IL-1α as potential therapeutic targets in ACLF, as well as other pyroptosis effector molecules, such as caspase 4 and caspase 5.

The invention claimed is:
1. A method of treating acute-on-chronic liver failure (ACLF) caused by aberrant pyroptosis in an individual in need thereof, said method comprising a step of administering to said individual an antagonist of GSDMD.

2. The method of claim 1, wherein the individual is suffering from, or is at risk of one or more of the following, when compared to a subject not suffering from ACLF:
- (a) renal dysfunction, and/or
- (b) renal failure, and/or
- (c) brain dysfunction, and/or
- (d) brain swelling, and/or
- (e) inflammation, injury or dysfunction in the kidney and/or brain, and/or
- (f) liver failure, and/or g immune failure.

3. The method of claim 1, wherein the antagonist of GSDMD is recombinant C-terminus GSDMD.

4. The method of claim 1, wherein the individual to be treated has an increased level of serum or plasma GSDMD compared to the level of GSDMD in the serum or plasma of an individual not suffering from ACLF.

5. The method of claim 1, wherein administration of said antagonist leads to:
- (a) decreased expression of GSDMD in the liver, immune cells, peripheral blood, kidney and/or brain of the individual; and/or
- (b) decreased levels of GSDMD in the liver, immune cells, peripheral blood, kidney and/or brain of the individual; and/or
- (c) decreased activity of GSDMD in the liver, immune cells, peripheral blood, kidney and/or brain of the individual.

6. The method of claim 1, wherein the antagonist is administered in combination with a further agent useful in the treatment of ACLF.

* * * * *